US009217136B2

(12) United States Patent
Palese et al.

(10) Patent No.: US 9,217,136 B2
(45) Date of Patent: Dec. 22, 2015

(54) CHIMERIC NEWCASTLE DISEASE VIRUSES AND USES THEREOF

(71) Applicants: MOUNT SINAI SCHOOL OF MEDICINE, New York, NY (US); MEMORIAL SLOAN-KETTERING CANCER CENTER, New York, NY (US)

(72) Inventors: Peter Palese, Leonia, NJ (US); Adolfo Garcia-Sastre, New York, NY (US); Dmitriy Zamarin, New York, NY (US); Yuman Fong, New York, NY (US)

(73) Assignees: Icahn School of Medicine at Mount Sinai, New york, NY (US); Memorial Sloan-Kettering Cancer Center, New York, NY (US)

( * ) Notice: Subject to any disclaimer, the term of this patent is extended or adjusted under 35 U.S.C. 154(b) by 55 days.

(21) Appl. No.: 14/060,166

(22) Filed: Oct. 22, 2013

(65) Prior Publication Data

US 2014/0044678 A1    Feb. 13, 2014

Related U.S. Application Data

(62) Division of application No. 13/147,842, filed as application No. PCT/US2010/023335 on Feb. 5, 2010, now Pat. No. 8,591,881.

(60) Provisional application No. 61/150,285, filed on Feb. 5, 2009.

(51) Int. Cl.
| | |
|---|---|
| *C12N 7/00* | (2006.01) |
| *C07K 14/005* | (2006.01) |
| *A61K 39/17* | (2006.01) |
| *A61K 35/13* | (2015.01) |

(52) U.S. Cl.
CPC ............... *C12N 7/00* (2013.01); *C07K 14/005* (2013.01); *A61K 35/13* (2013.01); *A61K 39/17* (2013.01); *C12N 2760/16122* (2013.01); *C12N 2760/18121* (2013.01); *C12N 2760/18122* (2013.01); *C12N 2760/18132* (2013.01); *C12N 2760/18143* (2013.01)

(58) Field of Classification Search
CPC .................. C07K 14/555; C12N 2710/16343; C12N 2710/24043; C12N 2750/14322; C12N 2770/24022; C12N 2710/16322; C12N 2710/16334; C12N 2740/15022; C12N 2760/18143; C12N 2760/18422; C12N 2760/18722; C12N 15/86; C12N 2760/18011; A61K 2039/5256; G01N 2333/115; G01N 33/6866
See application file for complete search history.

(56) References Cited

U.S. PATENT DOCUMENTS

| | | | |
|---|---|---|---|
| 5,166,057 A | 11/1992 | Palese et al. | |
| 5,786,199 A | 7/1998 | Palese | |
| 5,854,037 A | 12/1998 | Palese et al. | |
| 6,146,642 A | 11/2000 | Garcia-Sastre et al. | |
| 6,451,323 B1 | 9/2002 | Garcia-Sastre et al. | |
| 6,544,785 B1 | 4/2003 | Palese et al. | |
| 6,635,416 B2 | 10/2003 | Palese et al. | |
| 6,649,372 B1 | 11/2003 | Palese et al. | |
| 6,852,522 B1 | 2/2005 | Palese et al. | |
| 7,060,430 B2 | 6/2006 | Palese et al. | |
| 7,384,774 B2 | 6/2008 | Palese et al. | |
| 7,442,379 B2 | 10/2008 | Garcia-Sastre et al. | |
| 7,442,527 B2 | 10/2008 | Palese et al. | |
| 7,494,808 B2 | 2/2009 | Palese et al. | |
| 7,833,774 B2 | 11/2010 | Palese et al. | |
| 8,475,790 B2 | 7/2013 | Jure-kunkel | |
| 8,591,881 B2 * | 11/2013 | Palese et al. .................. | 424/93.3 |
| 2005/0191617 A1 | 9/2005 | Inoue et al. | |
| 2009/0061521 A1 | 3/2009 | Palese et al. | |
| 2009/0280144 A1 | 11/2009 | Garcia-Sastre et al. | |
| 2011/0189189 A1 | 8/2011 | Jure-kunkel | |
| 2012/0058141 A1 | 3/2012 | Palese et al. | |
| 2012/0058538 A1 | 3/2012 | Palese et al. | |
| 2012/0122185 A1 | 5/2012 | Palese et al. | |
| 2014/0044678 A1 | 2/2014 | Palese et al. | |
| 2014/0271677 A1 | 9/2014 | Palese et al. | |

FOREIGN PATENT DOCUMENTS

| | | |
|---|---|---|
| EP | 0702085 | 3/1996 |
| EP | 780475 | 6/1997 |
| EP | 0974660 A1 | 1/2000 |
| WO | WO 96/34625 | 11/1996 |
| WO | WO 97/06270 | 2/1997 |
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 99/66045 | 12/1999 |
| WO | WO 01/04333 | 1/2001 |

(Continued)

OTHER PUBLICATIONS

Verma et al. Nature, 1997, vol. 389, pp. 239-242.*
Houdebine L-M, Comparative Immunology, Microbiology and Infectious Disease 2009, vol. 32, pp. 107-121.*
Csatary et al., 2004, "MTH-68/H oncolytic viral treatment in human high-grade gliomas", J Neurooncol; 67:83-93.
De Leeuw et al., 2005, "Virulence of Newcastle disease virus is determined by the cleavage site of the fusion protein and by both the stem region and globular head of the haemagglutinin-neuraminidase protein", J Gen Virol; 86(5): 1759-1769.

(Continued)

*Primary Examiner* — Bao Li
(74) *Attorney, Agent, or Firm* — Jones Day

(57) ABSTRACT

Described herein are chimeric Newcastle disease viruses engineered to express a heterologous interferon antagonist and compositions comprising such viruses. The chimeric Newcastle disease viruses and compositions are useful in the treatment of cancer.

14 Claims, 15 Drawing Sheets

(56) References Cited

FOREIGN PATENT DOCUMENTS

Figure 1A:
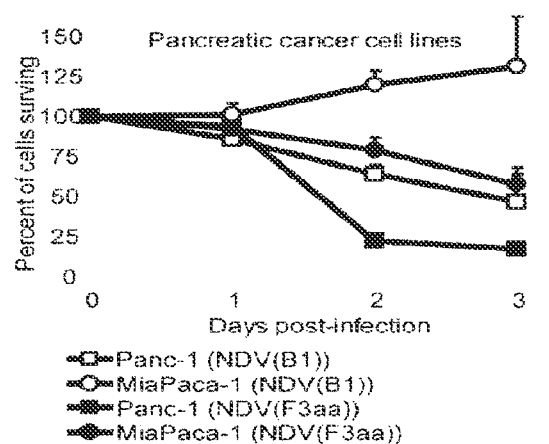
Figure 1A:
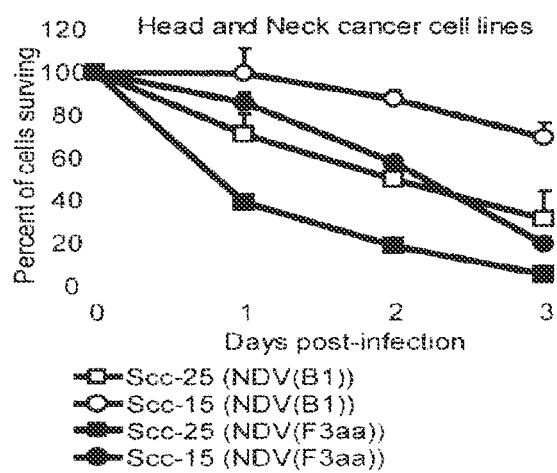
Figure 1A:
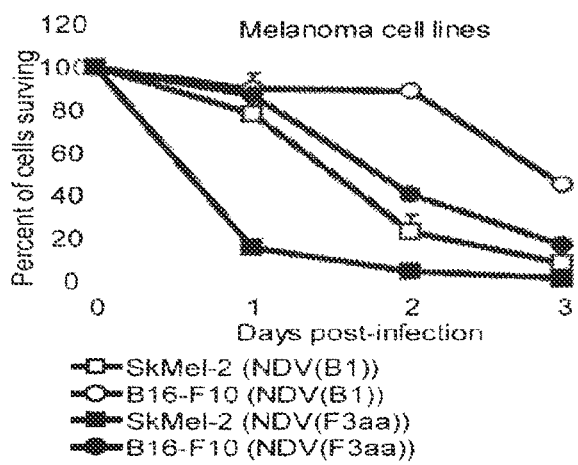

| | | |
|---|---|---|
| WO | WO 2007/064802 A1 | 6/2007 |
| WO | WO 2010/091262 | 8/2010 |
| WO | WO 2014/158811 | 10/2014 |

OTHER PUBLICATIONS

Dupraz et al., 2000, "Dominant negative MyD88 proteins inhibit interleukin-1β/interferon-γ-mediated induction of nuclear factor κB-dependent nitrite production and apoptosis in β cells", Journal of Biological Chemistry; 275:37672-37678.

Fiola et al., 2006, "Tumor selective replication of Newcastle disease virus: association with defects of tumor cells in antiviral defence", International Journal of Cancer 119(2): 328-338.

Foy et al., 2003, "Regulation of interferon regulatory factor-3 by the hepatitis C virus serine protease", Science ; 300(5622):1145-1148.

Freeman et al., 2006, "Phase I/II trial of intravenous NDV-HUJ oncolytic virus in recurrent glioblastoma multiforme", Molecular Therapy; 13: 221-228.

Hotte et al., 2007, "An optimized clinical regimen for the oncolytic virus PV701", Clin Cancer Res; 13:977-985.

International Search Report of International application No. PCT/US2010/023335, dated Jun. 7, 2010.

Krishnamurthy et al., 2006, "Differentially regulated interferon response determines the outcome of Newcastle disease virus infection in normal and tumor cell lines", Journal of Virology; 80:5145-5155.

Li et al, 2011, "Therapeutic effects of a fusogenic Newcastle disease virus in treating head and neck cancer", Head Neck; 33(10):1394-1399.

Lorence et al., 2007, "Phase 1 clinical experience using intravenous administration of PV701, an oncolytic Newcastle disease virus", Curr Cancer Drug Targets; 7:157-167.

Mansour et al., 2011, "Oncolytic specificity of newcastle disease virus is mediated by selectivity for apoptosis-resistant cells", J Virol; 85(12):6015-6023.

Nakaya et al., 2001, "Recombinant Newcastle disease virus as a vaccine vector", Journal of Virology; 75(23):11868-11873.

Park et al., 2003, "Newcastle disease virus V protein is a determinant of host range restriction", J Virol; 77(17):9522-9532.

Park et al., 2006, "Engineered viral vaccine constructs with dual specificity: avian influenza and Newcastle disease", Proc Natl Acad Sci USA; 103:8203-8208.

Pecora et al., 2002, "Phase I trial of intravenous administration of PV701, an oncolytic virus, in patients with advanced solid cancers", J Clin Oncol; 20:2251-2266.

Peeters et al., 1999, "Rescue of Newcastle disease virus from cloned cDNA: evidence that cleavability of the fusion protein is a major determinant for virulence", J Virol; 73(6):5001-5009.

Peeters et al., 2001, "Generation of a recombinant chimeric Newcastle disease virus vaccine that allows serological differentiation between vaccinated and infected animals", Vaccine; 19:1616-1627.

Phuangsab et al., 2001, "Newcastle disease virus therapy of human tumor xenografts: antitumor effects of local or systemic administration", Cancer Lett. 172:27-36.

Schirrmacher et al., 2001, "Antitumor effects of Newcastle Disease Virus in vivo: Local versus systemic effects", Int. J. Oncol.; 18:945-952.

Sharma et al., 2003, "Triggering the interferon antiviral response through an ikk-related pathway", Science; 300(5622):1148-1151.

Sinkovics et al., 2000, "Newcastle disease virus (NDV): brief history of its oncolytic strains", Journal of Clinical Virology; 16:1-15.

Swayne et al., 2003, "Recombinant paramyxovirus type 1-avian influenza-H7 virus as a vaccine for protection of chickens against influenza and Newcastle disease", Avian Disease; 743(3 Suppl):1047-1050.

Vigil et al., 2007, "Use of reverse genetics to enhance the oncolytic properties of Newcastle disease virus", Cancer Research; 67(17):8285-8292.

Vigil et al., 2008, "Recombinant Newcastle disease virus as a vaccine vector for cancer therapy", Molecular Therapy; 16(11):1883-1890.

Walter et al., 1997, "Targeted inhibition of interferon-dependent intercellular adhesion molecule-1 (ICAM-1) expression using dominant-negative stat1", J Biol Chem; 272(45):28582-28589.

Weber et al., 2007, "Viral suppression of the interferon system", Biochimie; 89(6-7):836-842.

Written Opinion of International application No. PCT/US2010/023335, dated Jun. 7, 2010.

Yoneyama et al., 2004, "The RNA helicase RIG-I has an essential function in double-stranded RNA-induced innate antiviral responses", Nature Immunology; 5:730-737.

Zamarin et al., 2009, "Enhancement of oncolytic properties of recombinant Newcastle disease virus through antagonism of cellular innate immune responses", Molecular Therapy: The Journal of the American Society of Gene Therapy; 17(4):697-706.

Zimmer et al., 2005, "A chimeric respiratory syncytial virus fusion protein functionally replaces the F and HN glycoproteins in recombinant sendai virus", J Virol; 79(16):10467-10477.

Alexander, 1988, "Newcastle disease, Newcastle disease virus—an avian paramyxovirus", Kluwer Academic Publishers, Dordrecht, The Netherlands, pp. 1-22.

Altomonte et al., 2010, "Engineered Newcastle disease virus as an improved oncolytic agent against hepatocellular carcinoma", Molecular Therapy, 18(2):275-284.

Bauzon and Hermiston, 2014, "Armed therapeutic viruses—a disruptive therapy on the horizon of cancer immunotherapy", Frontiers in Immunology, 5(74):doi: 10.3389/fimmu.2014.00074.

Bryant et al., 2000, "Development of intermediate-grade (mantle cell) and low-grade (small lymphocytic and marginal zone) human non-Hodgkin's lymphomas xenotransplanted in severe combined immunodeficiency mouse models", Lab. Invest. 80:557-573.

Dias et al., 2012, "Targeted cancer immunotherapy with oncolytic adenovirus coding for a fully human monoclonal antibody specific for CTLA-4", Gene Therapy, 19(10):988-998.

Elankumaran et al., 2010, "Type I interferon-sensitive recombinant newcastle disease virus for oncolytic vfrotherapy", J. Virol. 84:3835-3844.

Fecci et al., 2007, "Systemic CTLA-4 blockake ameliorates glioma-induced changes to the CD4+ T cell compartment without affecting regulatory T-cell function", Clin Cancer Res, 13(7):2158-2167.

Fodde and Smits, 2001, "Disease model: familial adenomatous polyposis", Trends Mol. Med. 7:369-373.

Fournier et al., 2013, "Oncolytic Newcastle Disease Virus as Cutting Edge between Tumor and Host", Biology, 2:936-975.

Fransen et al., 2013, "Controlled Local Delivery of CTLA-4 Blocking Antibody Induces CD8+ T-Cell-Dependent Tumor Eradication and Decreases Risk of Toxic Side Effects", Clinical Cancer Research, 19(19):5381-5389.

Gao et al., 2008, "Expression of transgenes from newcastle disease virus with a segmented genome" J Virol.; 82(6): 2692-2698.

Garcia-Sastre 1994, et al., "Use of a mammalian internal ribosomal entry site element for expression of a foreign protein by a transfectant influenza virus", J. Virol. 68:6254-6261.

Garcia-Sastre et al., 1994, "Introduction of foreign sequences into the genome of influenza A virus", Dev. Biol. Stand. 82:237-246.

GenBank Accession No. AF309418.1; Newcastle disease virus B1, complete genome; VRL Dec. 2, 2000.

GenBank Accession No. AY845400.2; Newcastle disease virus strain LaSota, complete genome; VRL Mar. 17, 2005.

GenBank Accession No. NC002617.1; Newcastle disease virus B1, complete genome, VRL Nov. 30, 2009.

Ghaneh et al., 2001, "Adenovirus-mediated transfer of p53 and p16(INK4a) results in pancreatic cancer regression in vitro and in vivo", Gene Ther. 8:199-208.

Guo et al., 2009, "Oncolytic immunotherapy: dying the right way is a key to eliciting potent antitumor immunity", Frontiers in Oncology, 4(74):1-11.

Hemminki et al., 2014, "Oncolytic Immunotherapy: Where Are We Clinically?", Scientifica, 2014, Article ID 862925.

Herber et al., 1996, "Squamous epithelial hyperplasia and carcinoma in mice transgenic for the human papillomavirus type 16 E7 oncogene", J. Virol. 70:1873-1881.

(56) References Cited

OTHER PUBLICATIONS

Hirschhorn-Cymerman et al., 2012, "Induction of tumoricidal function in CD4+ T cells is associated with concomitant memory and terminally differentiated phenotype", J Exp Med. 209(11):2113-2126.
Hosokawa et al., 2001, "In vivo analysis of mammary and non-mammary tumorigenesis in MMTV-cyclin D1 transgenic mice deficient in p53", Transgenic Res. 10:471-478.
Hough et al., 1998, "A model for spontaneous B-lineage lymphomas in IgHmu-HOX11 transgenic mice", Proc. Natl. Acad. Sci (USA) 95:13853-13858.
Huang et al. 2003, "Newcastle disease virus V protein is associated with viral pathogenesis and functions as an alpha interferon antagonist", J. Virol. 77:8676-8685.
Huard et al., 1995, "CD4/major histocompatibility complex class II interaction analyzed with CD4- and lymphocyte activation gene-3 (LAG-3)-Ig fusion proteins", Eur. J. Immunol. 25:2718-2721.
International Search Report dated Aug. 15, 2014 of International application No. PCT/US14/20299.
International Search Report dated Mar. 28, 2007 of International application No. PCT/US06/45859.
Kado et al., 2001, "Intestinal microflora are necessary for development of spontaneous adenocarcinoma of the large intestine in T-cell receptor beta chain and p53 double-knockout mice", Cancer Res. 61:2395-2398.
Khattar et al., 2009, "A Y526Q mutation in the Newcastle disease virus HN protein reduces its functional activities and attenuates virus replication and pathogenicity", J. Virol. 83:7779-7782.
Kim et al., 2001, "Expression and characterization of a recombinant Fab fragrant derived from an anti-human alpha-fetoprotein monoclonal antibody", Mol Cells, 11(2):158-163.
Kuraguchi et al., 2000, "Tumor-associated Apc mutations in M1h1 -/- Apc1638N mice reveal a mutational signature of M1h1 deficiency", Oncogene. 19(50):5755-5763.
Maeda et al., 2005, "Live bivalent vaccine for parainfluenza and influenza virus infections", J Virol, 79(11):6674-6679.
Meseck et al., 2011, "A Functional recombinant human 4-1BB ligand for immune costimulatory therapy of cancer", J. Immunother. 34:175-182.
Morris et al., 1998, "Lung-specific expression in mice of a dominant negative mutant form of the p53 tumor suppressor protein", J. LA State Med. Soc. 150:179-185.
Murawski et al., 2010, "Newcastle disease virus-like particles containing respiratory syncytial virus G protein induced protection in BALB/c mice, with no evidence of immunopathology", J Virol. 84(2):1110-1123.
Plitt and Zamarin, 2015, "Cancer therapy with Newcastle disease virus: rationale for new immunotherapeutic combinations", Clinical Investigation, 5(1), 75-87.
Puhler et al., 2008, "Generation of a recombinant oncolytic Newcastle disease virus and expression of a full IgG antibody from two transgenes", Gene Ther. 15:371-383, Epub Jan. 17, 2008.
Schickli et al., 2001, "Plasmid-only rescue of influenza A virus vaccine candidates", Phil Trans R Soc Lond, 356:1965-1973.
Schirrmacher and Fournier, 2009, "Newcastle disease virus: a promising vector for viral therapy, immune therapy, and gene therapy of cancer", Methods Mol Biol, 542:565-605.
Seppi et al., 1997, "Direct determination of oxygen by HPLC. 2. Chamber and sample application system for determination of o(2) at trace levels", Anal Chem. 69(21):4476-4481.
Silberhumer et al., 2010, "Genetically engineered oncolytic Newcastle disease virus effectively induces sustained remission of malignant pleural mesothelioma", Mol. Cancer Ther. 9(10):2761-2769.
Song et al., 2010, "Antitumor efficacy of viral therapy using genetically engineered Newcastle disease virus [NDV(F3aa)-GFP] for peritoneally disseminated gastric cancer", J Mol Med (Berl). 88(6):589-596.
Tuve et al., 2009, "In situ adenovirus vaccination engages T effector cells against cancer", Vaccine, 27:4225-4239.
Vail and MacEwen, 2000, "Spontaneously occurring tumors of companion animals as models for human cancer", Cancer Invest. 18:781-792.
Vigil et al., "Recombinant Newcastle disease virus as a vaccine vector for cancer therapy", Molecular Therapy, 16(11):1883-1890.
Wakamatsu et al., 2013, "Convergent and divergent effects of costimulatory molecules in conventional and regulatory CD4+ T cells", 110(3):1023-1028.
Wang et al., 2001, "A novel, clinically relevant animal model of metastatic pancreatic adenocarcinoma biology and therapy", Intl. J. Pancreatol. 29:37-46.
Woller et al., 2014, "Oncolytic viruses as anticancer vaccines", Frontiers in Oncology, 4(188):1-13.
Written Opinion dated Jul. 19, 2014 of International application No. PCT/US14/20299.
Written Opinion dated Mar. 28, 2007 of International application No. PCT/US06/45859.
Ying et al., 2011, "Adenovirus-mediated intratumoral expression of immunostimulatory proteins in combination with systemic Treg inactivation induces tumor-destructive immune responses in mouse models", Cancer Gene Ther:18(6):407-418.
Zamarin and Palese, 2012, "Oncolytic Newcastle disease virus for cancer therapy: old challenges and new directions", Future Microbiol. 7:347-367.
Zamarin and Wolchok, 2014, "Potentiation of immunomodulatory antibody therapy with oncolytic viruses for treatment of cancer", Molecular Therapy—Oncolytics, 1, 14004;10.1038/mto.2014.4.
Zamarin et al. 2009, "Genetically engineered Newcastle disease virus for malignant melanoma therapy", Gene Ther. 16(6):796-804.
Zamarin et al., 2014, "Localized oncolytic virotherapy overcomes systemic tumor resistance to immune checkpoint blockade immunotherapy", Sci. Transl. Med. 6(226):226ra32.
Zhang & Roth, 1994, "Anti-oncogene and tumor suppressor gene therapy—examples from a lung cancer animal model", In Vivo 8:755-769.

* cited by examiner

Replication of NDV(F3aa) and NDV(F3aa)-NS1 in Vero

□ NDV(F3aa) 0.001   ■ NDV(F3aa) 0.01
◇ NDV(F3aa)-NS1 0.001   ◆ NDV(F3aa)-NS1 0.01

Fig. 8

CHIMERIC NEWCASTLE DISEASE VIRUSES AND USES THEREOF

This application is divisional of U.S. patent application Ser. No. 13/147,842, filed Aug. 4, 2011, which is a national stage filing under 35 U.S.C. 371 of International Application No. PCT/US2010/023335, filed on Feb. 5, 2010, which claims priority to U.S. provisional application No. 61/150,285, filed Feb. 5, 2009, each of which is incorporated herein by reference in its entirety.

This invention was made, in part, with United States Government support under award numbers T32AI07647 and U54 AI057158 from the National Institutes of Health and Northeast Biodefense, respectively. The United States Government may have certain rights in this invention.

1. INTRODUCTION

Described herein are chimeric Newcastle disease viruses engineered to express a heterologous interferon antagonist and compositions comprising such viruses. The chimeric Newcastle disease viruses and compositions are useful in the treatment of cancer.

2. BACKGROUND

Newcastle Disease Virus (NDV) is a member of the *Avulavirus* genus in the Paramyxoviridae family, which has been shown to infect a number of avian species (Alexander, D J (1988). Newcastle disease, Newcastle disease virus—an avian paramyxovirus. Kluwer Academic Publishers Dordrecht, The Netherlands. pp 1-22). NDV possesses a single-stranded RNA genome in negative sense and does not undergo recombination with the host genome or with other viruses (Alexander, D J (1988). Newcastle disease, Newcastle disease virus—an avian paramyxovirus. Kluwer Academic Publishers: Dordrecht, The Netherlands. pp 1-22). The genomic RNA contains genes in the order of 3'-NP-P-M-F-HN-L-5', described in further detail below. Two additional proteins, V and W, are produced by NDV from the P gene by alternative mRNAs that are generated by RNA editing. The genomic RNA also contains a leader sequence at the 3' end.

The structural elements of the virion include the virus envelope which is a lipid bilayer derived from the cell plasma membrane. The glycoprotein, hemagglutinin-neuraminidase (HN) protrudes from the envelope allowing the virus to contain both hemagglutinin (e.g., receptor binding/fusogenic) and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication. The V protein has been shown to inhibit interferon-alpha and to contribute to the virulence of NDV (Huang et al. (2003). Newcastle disease virus V protein is associated with viral pathogenesis and functions as an Alpha Interferon Antagonist. *Journal of Virology* 77: 8676-8685).

Naturally-occurring NDV has been reported to be an effective oncolytic agent in a variety of animal tumor models (Sinkovics, J G, and Horvath, J C (2000). Newcastle disease virus (NDV): brief history of its oncolytic strains. *J Clin Virol* 16: 1-15). Naturally-occurring strains of NDV have been used in multiple clinical trials against advanced human cancers (Sinkovics, J G, and Horvath, J C (2000). Newcastle disease virus (NDV): brief history of its oncolytic strains. *J Clin Virol* 16: 1-15; Lorence et al. (2007). Phase 1 clinical experience using intravenous administration of PV701, an oncolytic Newcastle disease virus. *Curr Cancer Drug Targets* 7: 157-167; Hotte et al. (2007). An optimized clinical regimen for the oncolytic virus PV701. *Clin Cancer Res* 13: 977-985; Freeman et al. (2006). Phase I/II trial of intravenous NDV-HUJ oncolytic virus in recurrent glioblastoma multiforme. *Mol Ther* 13: 221-228; Pecora et al. (2002). Phase I trial of intravenous administration of PV701, an oncolytic virus, in patients with advanced solid cancers. *J Clin Oncol* 20: 2251-2266; Csatary et al. (2004). MTH-68/H oncolytic viral treatment in human high-grade gliomas. *J Neurooncol* 67: 83-93). However, the success of naturally-occurring strains of NDV in these clinical trials for advanced human cancers was only marginal (Hotte et al. (2007). An optimized clinical regimen for the oncolytic virus PV701. *Clin Cancer Res* 13: 977-985; Freeman et al. (2006). Phase I/II trial of intravenous NDV-HUJ oncolytic virus in recurrent glioblastoma multiforme. *Mol Ther* 13: 221-228; Pecora et al. (2002). Phase I trial of intravenous administration of PV701, an oncolytic virus, in patients with advanced solid cancers. *J Clin Oncol* 20: 2251-2266). As such, there remains a need for NDV-based therapies useful in the treatment of cancer, especially advanced cancer.

3. SUMMARY

In one aspect, presented herein are chimeric Newcastle disease viruses (NDVs) engineered to express a heterologous interferon antagonist. In a specific embodiment, presented herein are chimeric NDVs, comprising a packaged genome which encodes a heterologous interferon antagonist, wherein the heterologous interferon antagonist is expressed. In another embodiment, presented herein are chimeric NDVs, comprising a packaged genome which encodes a heterologous interferon antagonist and a modified F protein that causes the NDV to be highly fusogenic, wherein the heterologous interferon antagonist and the modified F protein are expressed. In another embodiment, presented herein are chimeric NDVs, comprising a packaged genome which encodes a heterologous interferon antagonist and a modified F protein with a mutated cleavage site, wherein the heterologous interferon antagonist and the modified F protein are expressed. In a specific embodiment, the chimeric NDVs expressing the modified F protein have increased fusogenic activity relative to the corresponding virus expressing the counterpart F protein without the mutations to the cleavage site. In another specific embodiment, the modified F protein is incorporated into the virion.

In another embodiment, presented herein are chimeric NDVs, comprising a packaged genome which encodes a heterologous interferon antagonist and a cytokine (e.g., interleukin (IL)-2), wherein the heterologous interferon antagonist and the cytokine are expressed. In another embodiment, presented herein are chimeric NDVs, comprising a packaged genome which encodes a heterologous interferon antagonist, a cytokine (e.g., IL-2) and a modified F protein that causes the NDV to be highly fusogenic, wherein the heterologous interferon antagonist, the cytokine and the modified F protein are expressed. In another embodiment, presented herein are chimeric NDVs, comprising a packaged genome which encodes a heterologous interferon antagonist, a cytokine (e.g., IL-2) and a modified F protein with a mutated cleavage site, wherein the heterologous interferon antagonist, the cytokine and the modified F protein are expressed. In another embodiment, presented herein are chimeric NDVs, comprising a packaged genome which encodes a heterologous interferon antagonist, a cytokine (e.g., IL-2) and a tumor antigen, wherein the heterologous interferon antagonist, the cytokine and the tumor antigen are expressed. In another embodiment, presented herein are chimeric NDVs, comprising a packaged genome which encodes a heterologous interferon antagonist, a cytokine (e.g., IL-2), a tumor antigen, and a modified F protein that causes the NDV to be highly fusogenic, wherein the heterologous interferon antagonist, the cytokine, the tumor antigen and the modified F protein are expressed. In another embodiment, presented herein are chimeric NDVs, comprising a packaged genome which encodes a heterologous interferon antagonist, a cytokine (e.g., IL-2), a tumor antigen, and a modified F protein with a mutated cleavage site, wherein the heterologous interferon antagonist, the cytokine, the tumor antigen and the modified F protein are expressed. In a specific embodiment, the chimeric NDVs expressing the modified F protein with the mutated cleavage site are highly fusogenic. In another specific embodiment, the modified F protein is incorporated into the virion.

In another embodiment, presented herein are chimeric NDVs, comprising a packaged genome which encodes a heterologous interferon antagonist and a tumor antigen, wherein the heterologous interferon antagonist and the tumor antigen are expressed. In another embodiment, presented herein are chimeric NDVs, comprising a packaged genome which encodes a heterologous interferon antagonist, a tumor antigen and a modified F protein that causes the NDV to be highly fusogenic, wherein the heterologous interferon antagonist, the tumor antigen and the modified F protein are expressed. In another embodiment, presented herein are chimeric NDVs, comprising a packaged genome which encodes a heterologous interferon antagonist, a tumor antigen and a modified F protein with a mutated cleavage site, wherein the heterologous interferon antagonist, the tumor antigen and the modified F protein are expressed. In a specific embodiment, the chimeric NDVs expressing the modified F protein with the mutated cleavage site are highly fusogenic. In another specific embodiment, the modified F protein is incorporated into the virion.

In a specific embodiment, the heterologous interferon antagonist is a viral protein. Specific examples of viral proteins that are interferon antagonists include, but are not limited to, Nipah virus W protein, Nipah V protein, Ebola virus VP35 protein, vaccinia virus E3L protein, influenza virus NS1 protein, respiratory syncytial virus (RSV) NS2 protein, herpes simplex virus (HSV) type 1 ICP34.5 protein, and Hepatitis C virus NS3-4 protease. In a specific embodiment, the viral protein is an influenza virus NS1 protein. In another embodiment, the heterologous interferon antagonist is a cellular protein. Specific examples of such cellular proteins include, but are not limited to, dominant-negative cellular proteins that block the induction or response to innate immunity and cellular regulators of the innate immune response.

In another aspect, presented herein are methods for propagating the chimeric NDVs described herein. The chimeric NDVs described herein can be propagated in any cell, subject, tissue or organ susceptible to a NDV infection. In one embodiment, the chimeric NDVs described herein may be propagated in a cell line. In another embodiment, the chimeric NDVs described herein may be propagated in cancer cells. In another embodiment, the chimeric NDVs described herein may be propagated in an embryonated egg. In certain embodiments, presented herein are isolated cells, tissues or organs infected with a chimeric NDV described herein. See, e.g., Section 5.3 for examples of cells, animals and eggs to infect with a chimeric NDV described herein. In specific embodiments, presented herein are isolated cancer cells infected with a chimeric NDV described herein. In certain embodiments, presented herein are cell lines infected with a chimeric NDV described herein. In other embodiments, presented herein are embryonated eggs infected with a chimeric NDV described herein.

In another aspect, presented herein are compositions comprising a chimeric NDV described herein. In a specific embodiment, presented herein are pharmaceutical compositions comprising a chimeric NDV described herein and a pharmaceutically acceptable carrier. In another embodiment, presented herein are pharmaceutical compositions comprising cancer cells infected with a chimeric NDV described herein, and a pharmaceutically acceptable carrier. In specific embodiments, the cancer cells have been treated with gamma radiation prior to incorporation into the pharmaceutical composition. In specific embodiments, the cancer cells have been treated with gamma radiation before infection with chimeric NDV. In other specific embodiments, the cancer cells have been treated with gamma radiation after infection with chimeric NDV. In another embodiment, presented herein are pharmaceutical compositions comprising protein concentrate from lysed chimeric NDV-infected cancer cells, and a pharmaceutically acceptable carrier.

In another aspect, presented herein are methods for producing pharmaceutical compositions comprising a chimeric NDV described herein. In one embodiment, a method for producing a pharmaceutical composition comprises: (a) propagating a chimeric NDV described herein in a cell line that is susceptible to a NDV infection; and (b) collecting the progeny virus, wherein the virus is grown to sufficient quantities and under sufficient conditions that the virus is free from contamination, such that the progeny virus is suitable for formulation into a pharmaceutical composition. In another embodiment, a method for producing a pharmaceutical composition comprises: (a) propagating a chimeric NDV described herein in an embryonated egg; and (b) collecting the progeny virus, wherein the virus is grown to sufficient quantities and under sufficient conditions that the virus is free from contamination, such that the progeny virus is suitable for formulation into a pharmaceutical composition.

In another aspect, presented herein are methods for treating cancer utilizing a chimeric NDV described herein or a pharmaceutical composition comprising such a chimeric NDV. In a specific embodiment, a method for treating cancer comprises infecting a cancer cell in a subject with a chimeric NDV described herein or a pharmaceutical composition thereof. In another embodiment, a method for treating cancer comprises administering to a subject in need thereof a chimeric NDV described herein or a pharmaceutical composition thereof. In certain embodiments, two or more chimeric NDVs are administered to a subject to treat cancer.

In another embodiment, a method for treating cancer comprises administering to a subject in need thereof cancer cells infected with a chimeric NDV described herein or a pharmaceutical composition thereof. In specific embodiments, the cancer cells have been treated with gamma radiation prior to administration to the subject or incorporation into the pharmaceutical composition. In another embodiment, a method for treating cancer comprises administering to a subject in need thereof a protein concentrate or plasma membrane fragments from cancer cells infected with a chimeric NDV or a pharmaceutical composition thereof.

3.1 Terminology

As used herein, the term "about" or "approximately" when used in conjunction with a number refers to any number within 1, 5 or 10% of the referenced number.

As used herein, the term "interferon antagonist" refers to an agent that reduces or inhibits the cellular interferon immune response. In one embodiment, an interferon antagonist is a proteinaceous agent that reduces or inhibits the cellular interferon immune response. In a specific embodiment, an interferon antagonist is a viral protein or polypeptide that reduces or inhibits the cellular interferon response.

In a specific embodiment, an interferon antagonist is an agent that reduces or inhibits interferon expression and/or activity. In one embodiment, the interferon antagonist reduces or inhibits the expression and/or activity of type I IFN. In another embodiment, the interferon antagonist reduces or inhibits the expression and/or activity of type II IFN. In another embodiment, the interferon antagonist reduces or inhibits the expression and/or activity of type III IFN. In a specific embodiment, the interferon antagonist reduces or inhibits the expression and/or activity of either IFN-α, IFN-β or both. In another specific embodiment, the interferon antagonist reduces or inhibits the expression and/or activity of IFN-γ. In another embodiment, the interferon antagonist reduces or inhibits the expression and/or activity of one, two or all of IFN-α, IFN-β, and IFN-γ.

In certain embodiments, the expression and/or activity of IFN-α, IFN-β and/or IFN-γ in an embryonated egg or cell is reduced approximately 1 to approximately 100 fold, approximately 5 to approximately 80 fold, approximately 20 to approximately 80 fold, approximately 1 to approximately 10 fold, approximately 1 to approximately 5 fold, approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by an interferon antagonist relative to the expression and/or activity of IFN-α, IFN-β, and/or IFN-γ in a control embryonated egg or a cell not expressing or not contacted with such an interferon antagonist as measured by the techniques described herein or known to one skilled in the art. In other embodiments, the expression and/or activity of IFN-α, IFN-β and/or IFN-γ in an embryonated egg or cell is reduced by at least 20% to 25%, at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80% to 85%, at least 85% to 90%, at least 90% to 95%, at least 95% to 99% or by 20%, 25%, 30%, 35%, 40%, 45%, 50%, 55%, 60%, 65%, 70%, 75%, 80%, 85%, 90%, 95%, or 99% by an interferon antagonist relative to the expression and/or activity of IFN-α, IFN-β, and/or IFN-γ in a control embryonated egg or a cell not expressing or not contacted with such an interferon antagonist as measured by the techniques described herein or known to one skilled in the art.

As used herein, the term "heterologous interferon antagonist" refers to an interferon antagonist that is not found in nature to be associated with the genome of the chimeric NDV backbone.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human toddler" refers to a human that is 1 year to 3 years old.

As used herein, the term "human infant" refers to a newborn to 1 year old year human.

In certain embodiments, the terms "highly fusogenic" and "increased fusogenic activity", and the like, as used herein, refers to an increase in the ability of the NDV to form syncytia involving a large number of cells. In a specific embodiment, cells infected with a chimeric NDV described herein that is engineered to express a modified F protein have an increased ability to form syncytia relative to cells infected with the parental virus from which the chimeric virus is derived which has an unmodified F protein. In another specific embodiment, about 10% to about 25%, about 25% to about 50%, about 25% to about 75%, about 50% to about 75%, about 50% to about 95%, or about 75% to about 99% or about 10%, 15%, 20%, 25%, 30%, 35%, 40%, 45%, 50%, 55%, 60%, 65%, 70%, 75%, 80%, 85%, 90%, 95%, or 99% more cells infected with a chimeric NDV described herein that is engineered to express a modified F protein form syncytia relative to the number of cells forming syncytia that are infected with the parental virus from the chimeric virus is derived which has an unmodified F protein. In certain embodiments, the syncytia are quantitated microscopically by counting the number of nuclei per syncytium after a certain period of time (e.g., about 8 hours to about 12 hours, about 12 hours to about 24 hours, about 24 hours to about 36 hours, or about 36 hours to about 48 hours).

As used herein, the phrases "IFN deficient systems" or "IFN-deficient substrates" refer to systems, e.g., cells, cell lines and animals, such as mice, chickens, turkeys, rabbits, rats, horses etc., which do not produce one, two or more types of IFN, or do not produce any type of IFN, or produce low levels of one, two or more types of IFN, or produce low levels of any IFN (i.e., a reduction in any IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to one, two or more types of IFN, or do not respond to any type of IFN, have a delayed response to one, two or more types of IFN, and/or are deficient in the activity of antiviral genes induced by one, two or more types of IFN, or induced by any type of IFN.

As used herein, the phrase "multiplicity of infection" or "MOI" is the average number of virus per infected cell. The MOI is determined by dividing the number of virus added (ml added×Pfu) by the number of cells added (ml added×cells/ml).

As used herein, the terms "subject" or "patient" are used interchangeably. As used herein, the terms "subject" and "subjects" refers to an animal. In some embodiments, the subject is a mammal including a non-primate (e.g., a camel, donkey, zebra, cow, horse, horse, cat, dog, rat, and mouse) and a primate (e.g., a monkey, chimpanzee, and a human). In some embodiments, the subject is a non-human mammal. In certain embodiments, the subject is a pet (e.g., dog or cat) or farm animal (e.g., a horse, pig or cow). In other embodiments the subject is a human. In certain embodiments, the mammal (e.g., human) is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In specific embodiments, the subject is an animal that is not avian.

As used herein, the terms "treat" and "treating" in the context of the administration of a therapy refers to a treatment/therapy from which a subject receives a beneficial effect, such as the reduction, decrease, attenuation, diminishment, stabilization, remission, suppression, inhibition or arrest of the development or progression of cancer, or a symptom thereof. In certain embodiments, the treatment/therapy that a subject receives results in at least one or more of the following effects: (i) the reduction or amelioration of the severity of cancer and/or a symptom associated therewith; (ii) the reduction in the duration of a symptom associated with cancer; (iii) the prevention in the recurrence of a symptom associated with cancer; (iv) the regression of cancer and/or a symptom associated therewith; (v) the reduction in hospitalization of a subject; (vi) the reduction in hospitalization length; (vii) the increase in the survival of a subject; (viii) the inhibition of the progression of cancer and/or a symptom associated therewith; (ix) the enhancement or improvement the therapeutic effect of another therapy; (x) a reduction or elimination in the cancer cell population; (xi) a reduction in the growth of a tumor or neoplasm; (xii) a decrease in tumor size; (xiii) a reduction in the formation of a tumor; (xiv) eradication, removal, or control of primary, regional and/or metastatic cancer; (xv) a decrease in the number or size of metastases; (xvi) a reduction in mortality; (xvii) an increase in cancer-free survival rate of patients; (xviii) an increase in relapse-free survival; (xix) an increase in the number of patients in remission; (xx) a decrease in hospitalization rate; (xxi) the size of the tumor is maintained and does not increase in size or increases the size of the tumor by less 5% or 10% after administration of a therapy as measured by conventional methods available to one of skill in the art, such as MRI, X-ray, and CAT Scan; (xxii) the prevention of the development or onset of cancer and/or a symptom associated therewith; (xxiii) an increase in the length of remission in patients; (xxiv) the reduction in the number of symptoms associated with cancer; (xxv) an increase in symptom-free survival of cancer patients; and/or (xxvi) limitation of or reduction in metastasis. In some embodiments, the treatment/therapy that a subject receives does not cure cancer, but prevents the progression or worsening of the disease. In certain embodiments, the treatment/therapy that a subject receives does not prevent the onset/development of cancer, but may prevent the onset of cancer symptoms.

As used herein, the term "in combination" in the context of the administration of (a) therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the terms "therapies" and "therapy" can refer to any protocol(s), method(s), and/or agent(s) that can be used in the treatment of cancer. In certain embodiments, the terms "therapies" and "therapy" refer to biological therapy, supportive therapy, hormonal therapy, chemotherapy, immunotherapy and/or other therapies useful in the treatment of cancer. In a specific embodiment, a therapy includes adjuvant therapy. For example, using a therapy in conjunction with a drug therapy, biological therapy, surgery, and/or supportive therapy. In certain embodiments, the term "therapy" refers to a chimeric NDV described herein. In other embodiments, the term "therapy" refers to an agent that is not a chimeric NDV.

4. BRIEF DESCRIPTION OF THE FIGURES

Figure 1B:
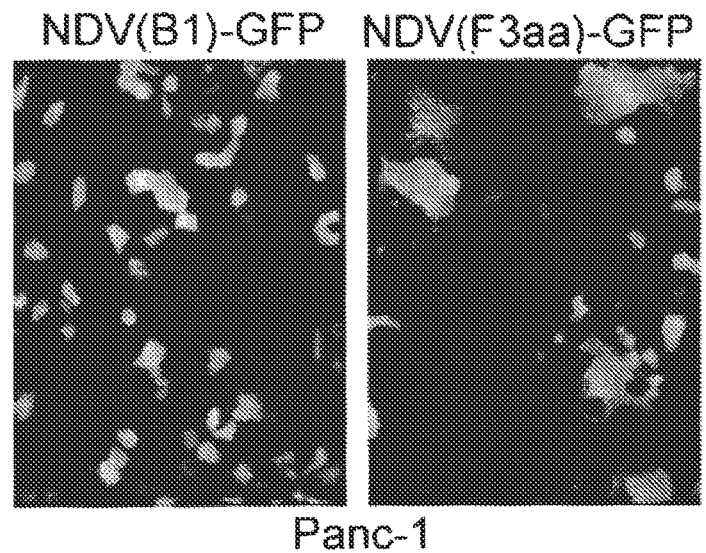
Figure 1B:
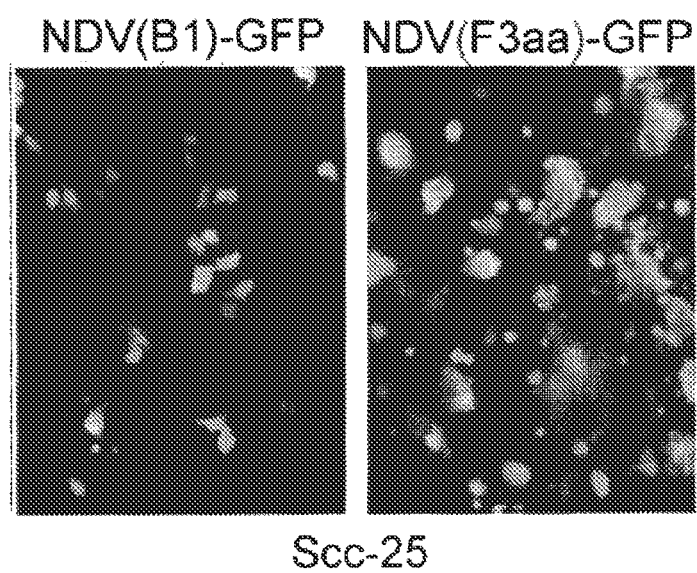

FIGS. 1A-1B. Recombinant NDV with modified fusion protein induces enhanced cytolysis in multiple human cancer cell lines. (A). Cell lines ($5 \times 10^5$ cells) were infected at MOI 0.1 in triplicate and LDH release assays were performed at 24, 48, and 72 hours. Percentage of cells surviving at 24, 48, and 72 hours is shown. (B). Syncytia formation by the NDV (F3aa) virus. Cell lines tested in (a) were infected with NDV (B1)-GFP and NDV(F3aa)-GFP at MOI 0.01, stained with Hoechst after 24 hours and images were taken under fluorescent microscope. Representative images from Panc-1, and Scc-25 cells are shown (green: GFP).

Figure 2A:
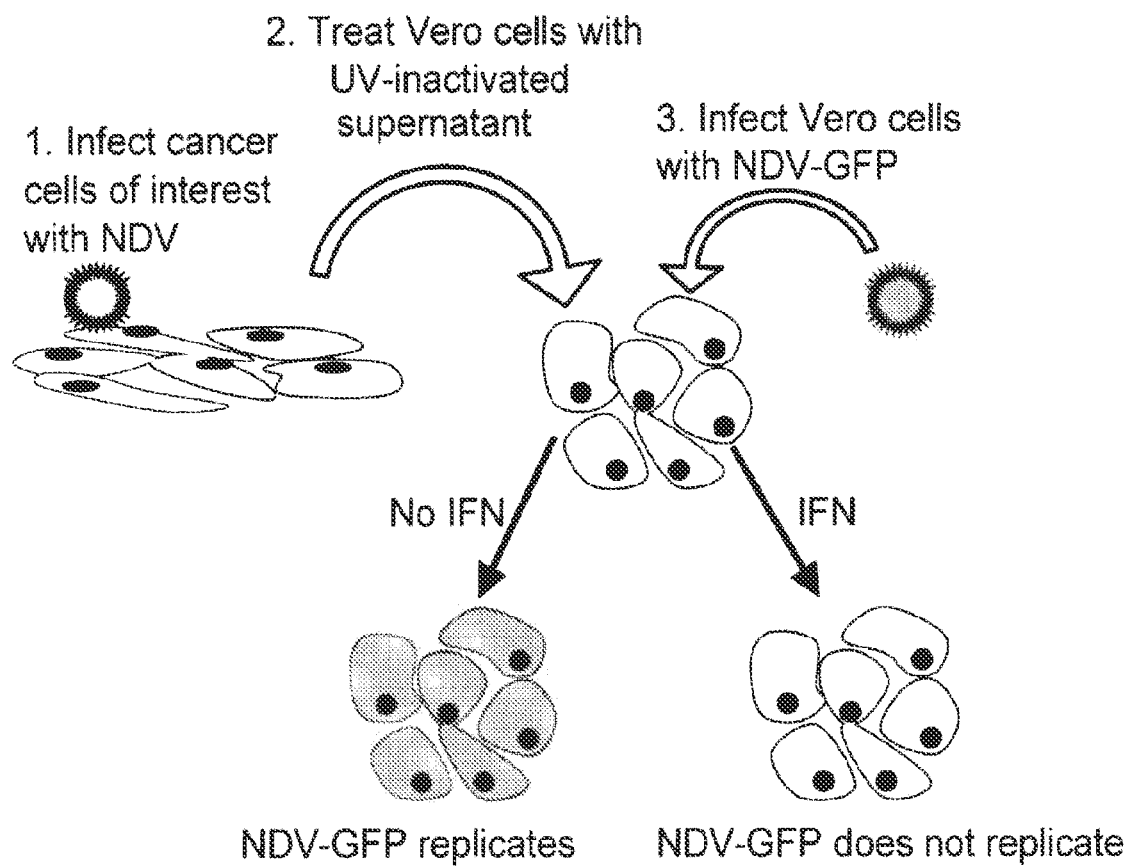
Figure 2B:
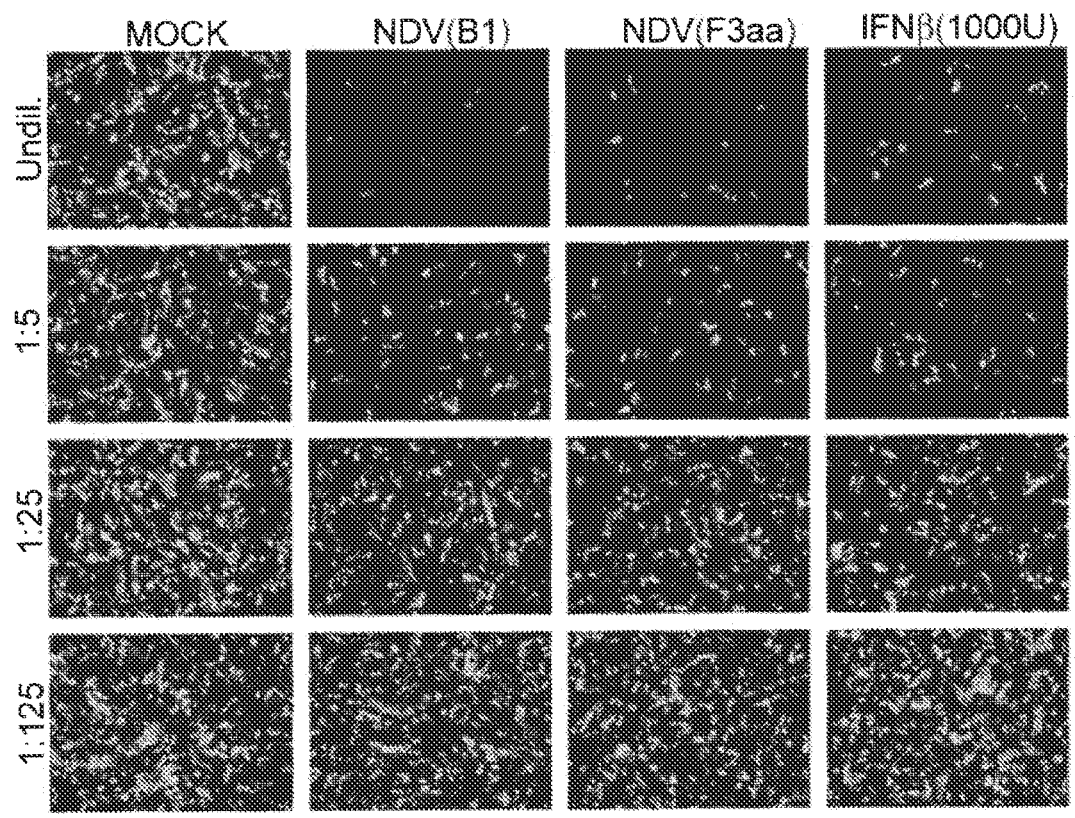
Figure 4A:
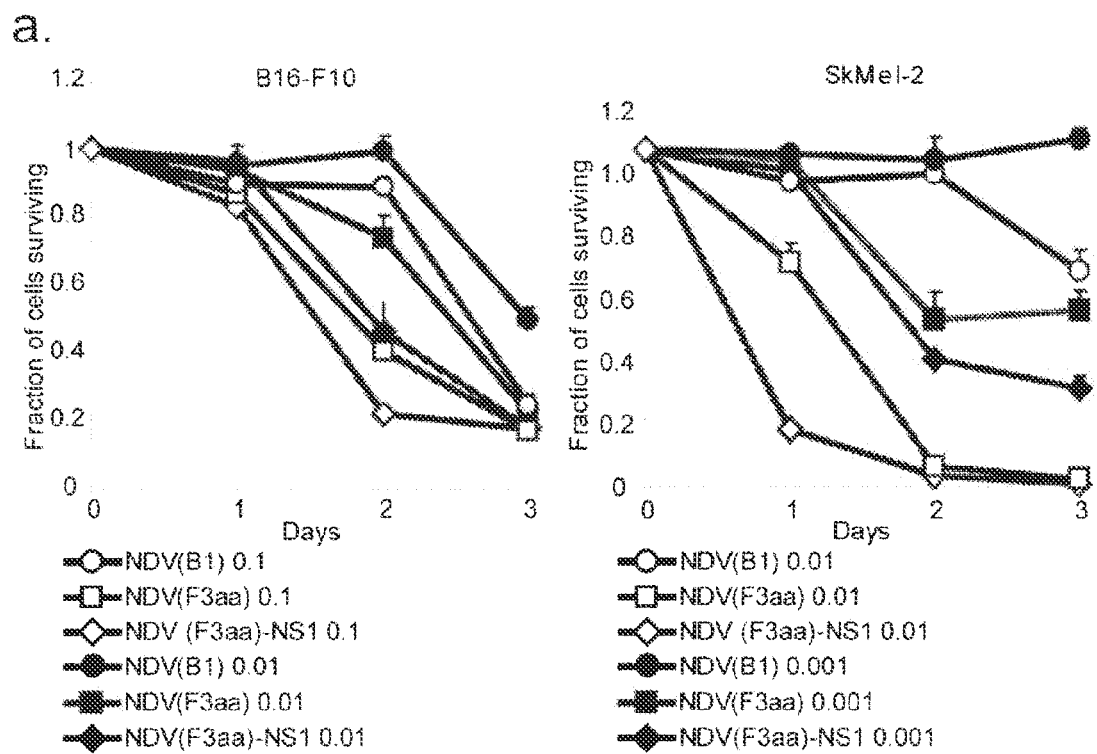
Figure 4B:
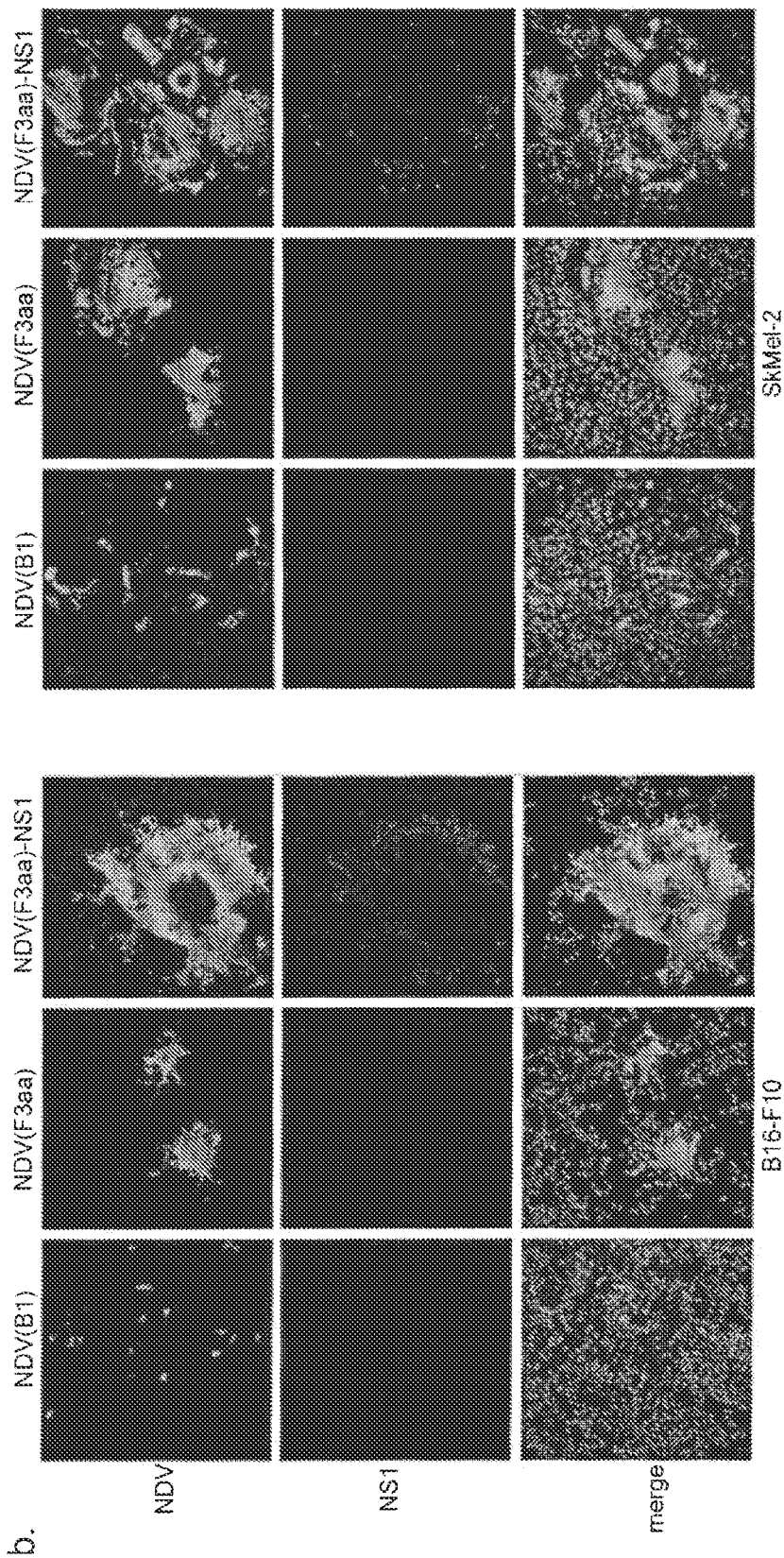
Figure 4C:
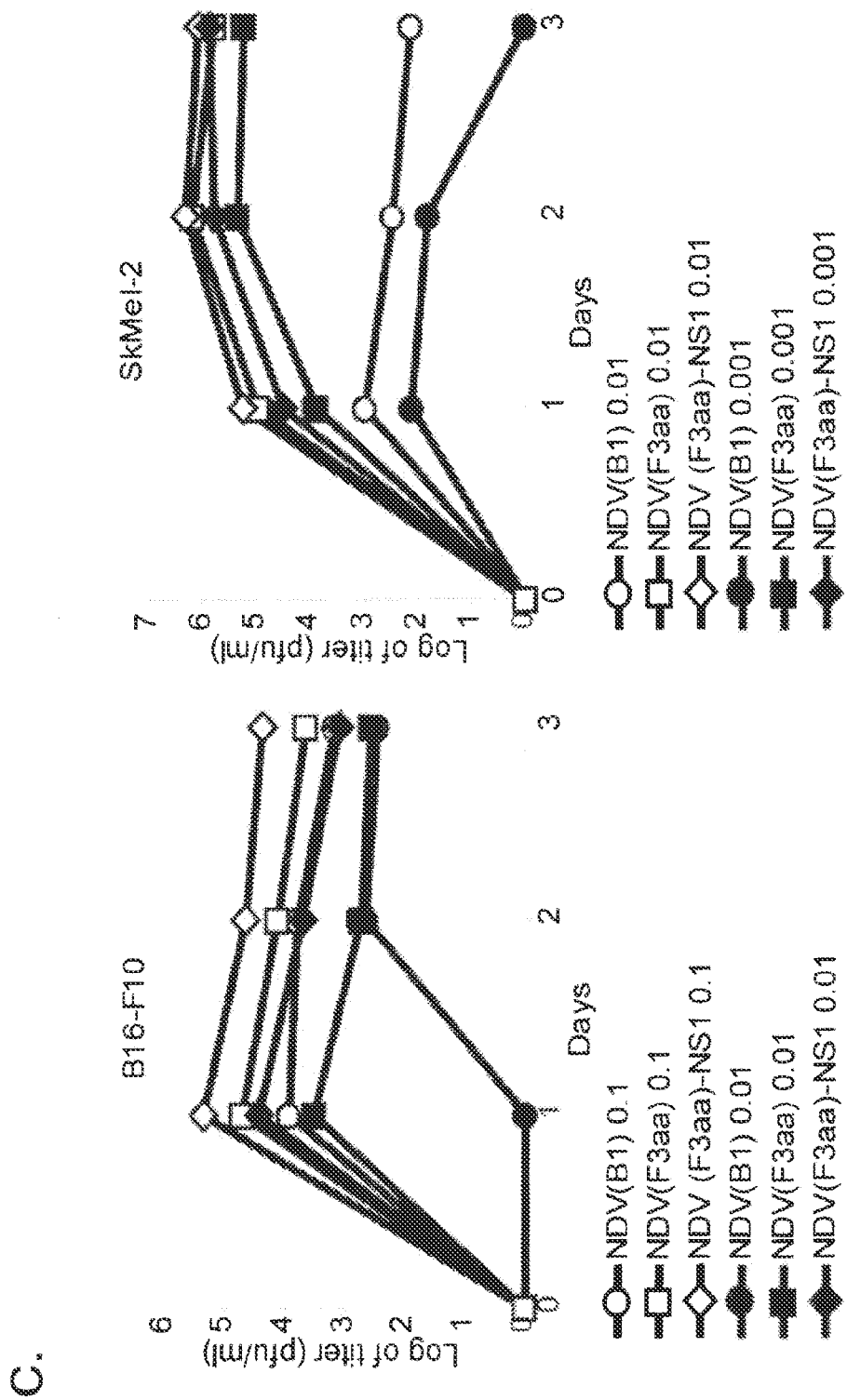
Figure 4D:
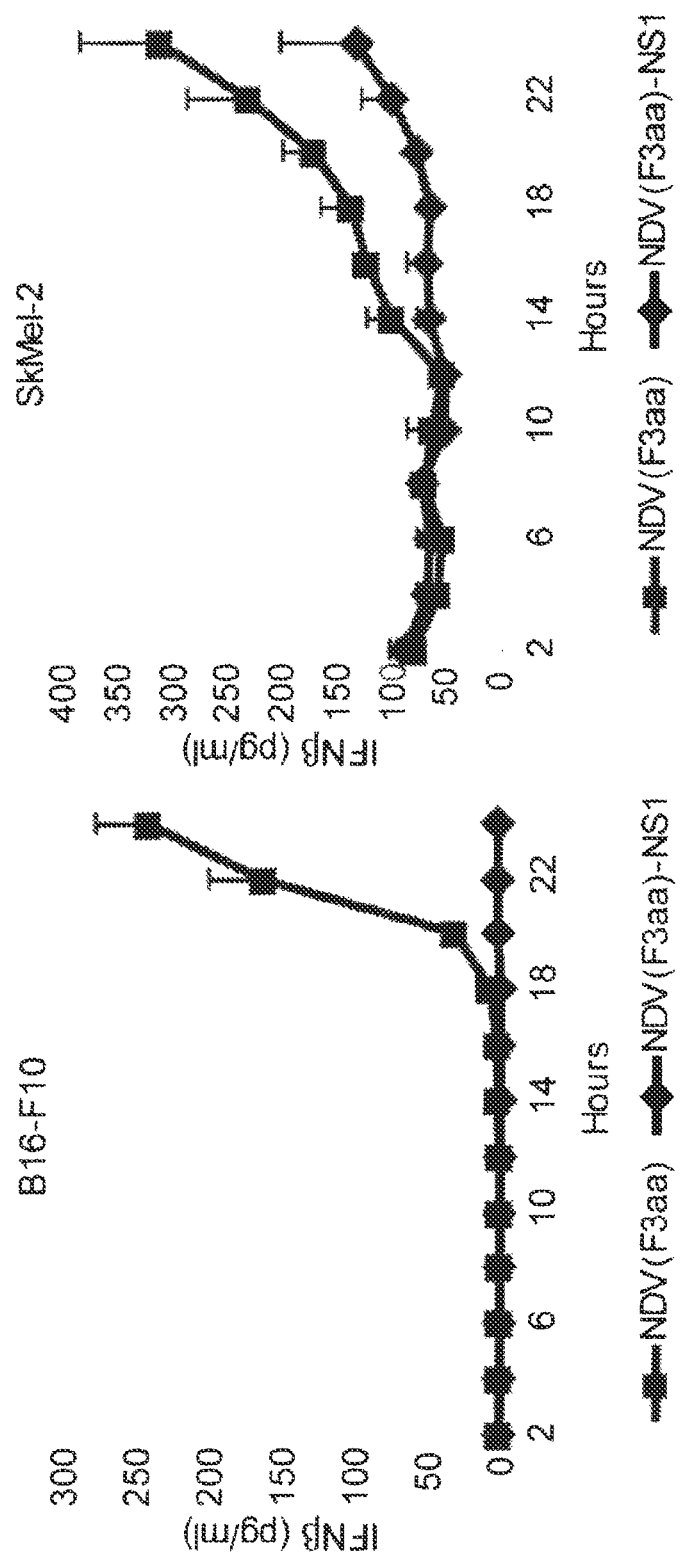

FIGS. 2A-2B. NDV induces antiviral response in the infected cancer cells. (A). Schematic diagram of the bioassay for IFN production. Panc-1 cells were infected with NDV viruses at MOI 0.1. Supernatants were collected at 24 hours, and any virus present was UV inactivated. Fresh Vero cells were treated with the inactivated supernatants and then infected with NDV-GFP at MOI of 0.1. (B). Antiviral activity in the infected Panc-1 supernatants. Supernatants were diluted in 5-fold series. Supernatants from non-infected cells and recombinant human IFNβ were used as negative and positive controls respectively. NDV-GFP-infected Vero cells were examined by fluorescence microscopy.

Figures 3A, 3B:
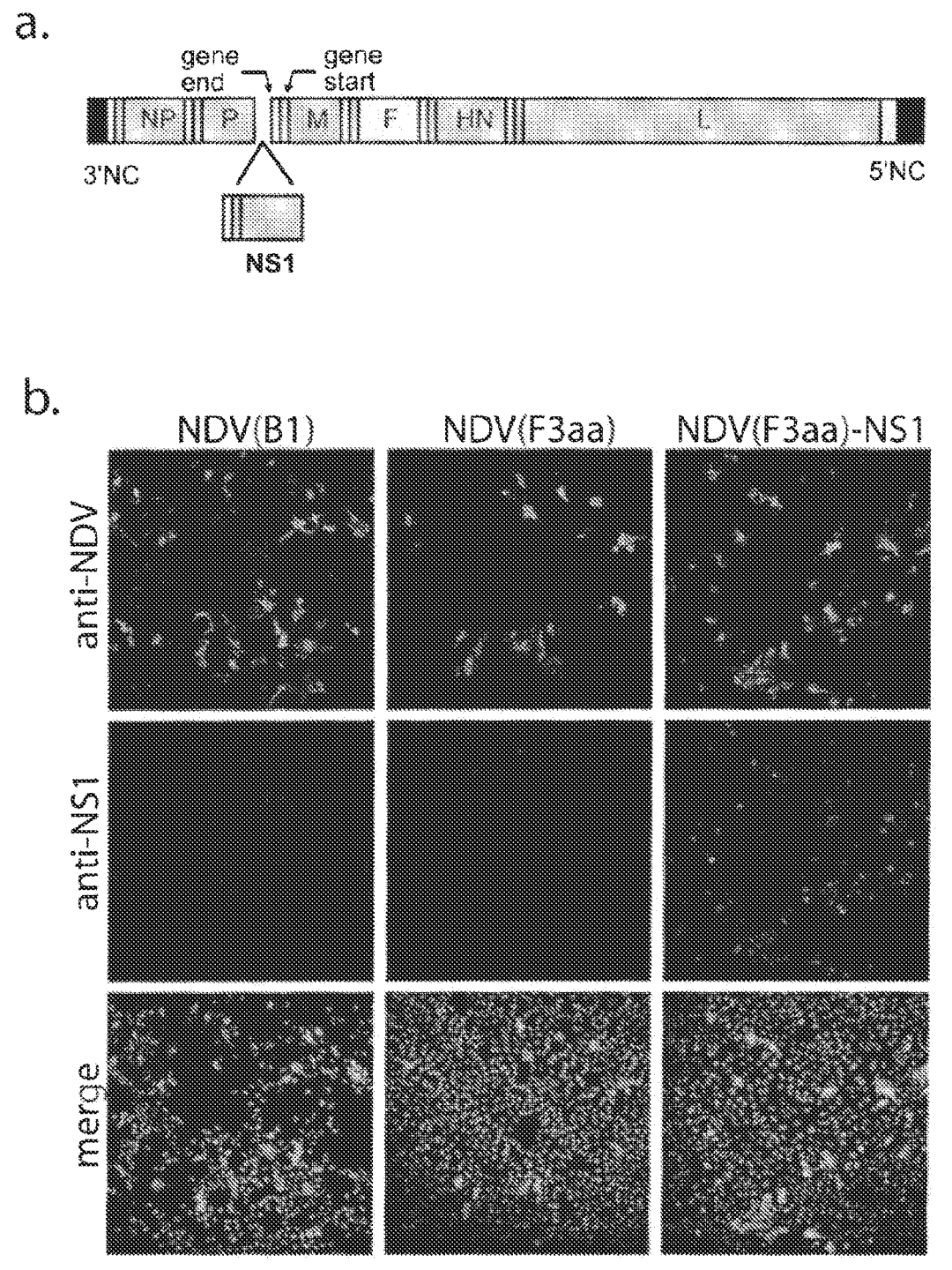
Figure 3C:
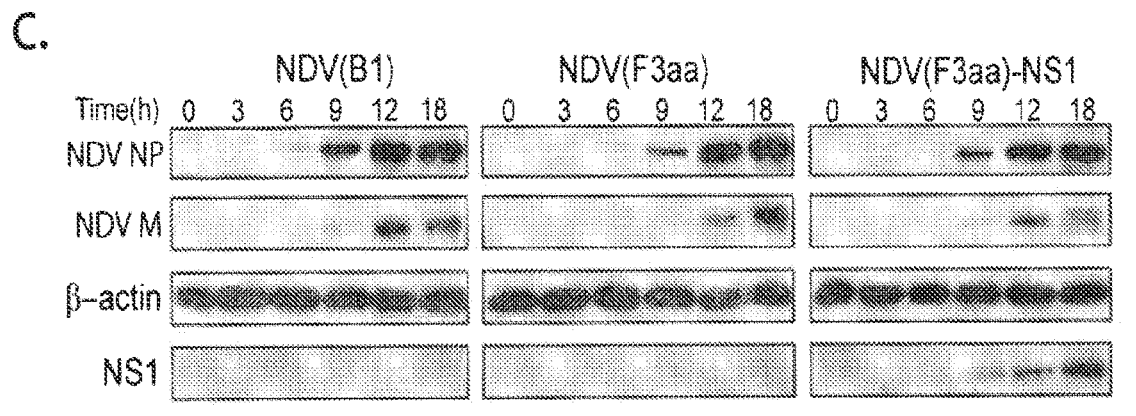

FIGS. 3A-3C. Generation of NDV(F3aa)-NS1 virus. (A). Schematic diagram of the generated NDV(F3aa)-NS1 virus genome. (B). Expression of the NS1 protein in NDV(F3aa)-NS1-infected Vero cells. Cells were infected at MOI 0.01, fixed at 18 hours post-infection, and stained with Dapi (blue), anti-NDV rabbit polyclonal antibody (green) and anti-NS1 mouse monoclonal antibody (red). NDV(B1) and NDV (F3aa)-infected cells were used as negative controls. (C). Time course of NS1 protein expression. Vero cells were infected with appropriate viruses at MOI 0.1 and collected at the indicated time points. Cells were lysed and analyzed by immunoblotting with antibodies to β-actin, NDV proteins, and influenza NS1.

FIGS. 4A-4D. NDV(F3aa)-NS1 virus replicates and induces oncolysis in human and mouse melanoma cell lines. (A). Cytotoxicity of the genetically-engineered NDV in B16-F10 and SkMel-2 cells. B16-F10 cells (left panel) and SkMel-2 cells (right panel) were infected with NDV(B1), NDV(F3aa), and NDV(F3aa)-NS1 viruses at the indicated MOI's. Cytotoxicity was assessed at 24, 48, and 72 hours by LDH release assays. Lower MOI's were used in SkMel-2 cells due to higher susceptibility of the cells to NDV. (B). Efficiency of syncytia formation by the recombinant viruses. B16-F10 and SkMel-2 cells were infected with appropriate viruses at MOI 0.001 for 18 hours, and fixed and stained for NDV(green), NS1(red), and Dapi (blue). (C). Replication of NDV in B16-F10 and SkMel-2 cell lines. Cells were infected at the indicated MOI's and the supernatants were collected at 24, 48, and 72 hours. (D). IFNβ induction in B16-F10 and SkMel-2 cells. Cells were infected with the indicated virus at MOI 1 and the supernatants were collected every 2 hours for 24 hours. Levels of IFNβ in the supernatant were assessed by murine and human IFNβ ELISA.

FIGS. 5A-5D. NDV(F3aa)-NS1 suppresses tumor growth and promotes mouse survival in a syngeneic murine melanoma model. (A). Short-term tumor growth in B16-F10 melanoma-bearing mice treated with recombinant NDV viruses at 7 days. Mice were injected in the right posterior foot pad with 105 of cultured B16-F10 cells, and 7 days later were treated with 5×106 of the indicated viruses or PBS for a total of 4 injections. All 8 mice from the control group and 6 randomly-chosen mice from each virus group were sacrificed on day 25 for immune studies (see FIG. 6). (B). Short-term tumor growth in mice treated at 10 days. Starting on day 10 after tumor cell line injection, the mice were treated every other day with a total of 6 doses of 5×106 pfu of the indicated virus or PBS. When the largest tumors reached 8 mm in length, all of the animals were sacrificed. (C). Long-term tumor growth follow-up in the treated mice. The remaining 7 animals from each group in (A) were continued to be followed for 120 days, with tumor measurements being recorded every 2 days. (D). Summary of 120-day survival of the animals treated in (A). Mice were sacrificed when the tumors reached 8 mm in length. For experimental groups, only the mice included in the long-term study (n=7 for each group) were included in the analysis ($*p<1×10^{-6}$).

Figures 6A, 6B, 6C:
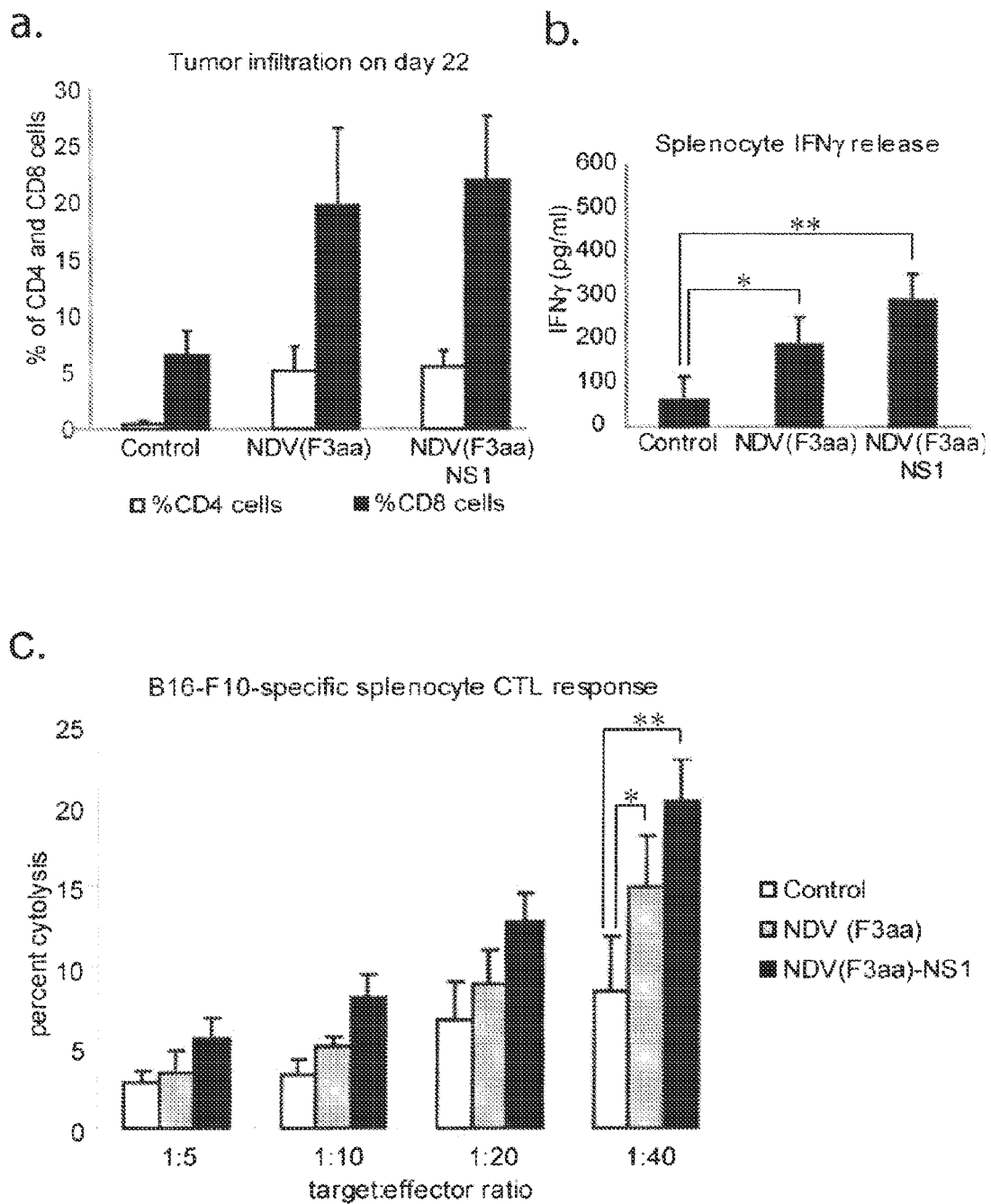

FIGS. 6A-6C. NDV treatment leads to tumor lymphocyte infiltration and generation of anti-melanoma immune responses. (A). Tumor infiltration with CD4+ and CD8+ cells. Tumors collected from the animals described in 6D were dissociated into single-cell suspensions and analyzed by flow cytometry for presence of CD4 and CD8 cells. (B). IFNγ release from stimulated splenocytes. Splenocytes collected from the sacrificed animals in 6a were co-cultured with mitomycin-inactivated B16-F10 cells and IFNγ was measured in the supernatants on day 3 of co-culture ($*p<0.003$, $**p<0.00006$). (C). Melanoma-specific cytotoxicity of the stimulated splenocytes. Stimulated splenocytes described in (b) were co-cultured with fresh B16-F10 cells for 4 hours at the indicated ratios and specific cytotoxic activity was determined by measurements of LDH release ($*p<0.015$, $**p<0.0007$).

Figure 7:
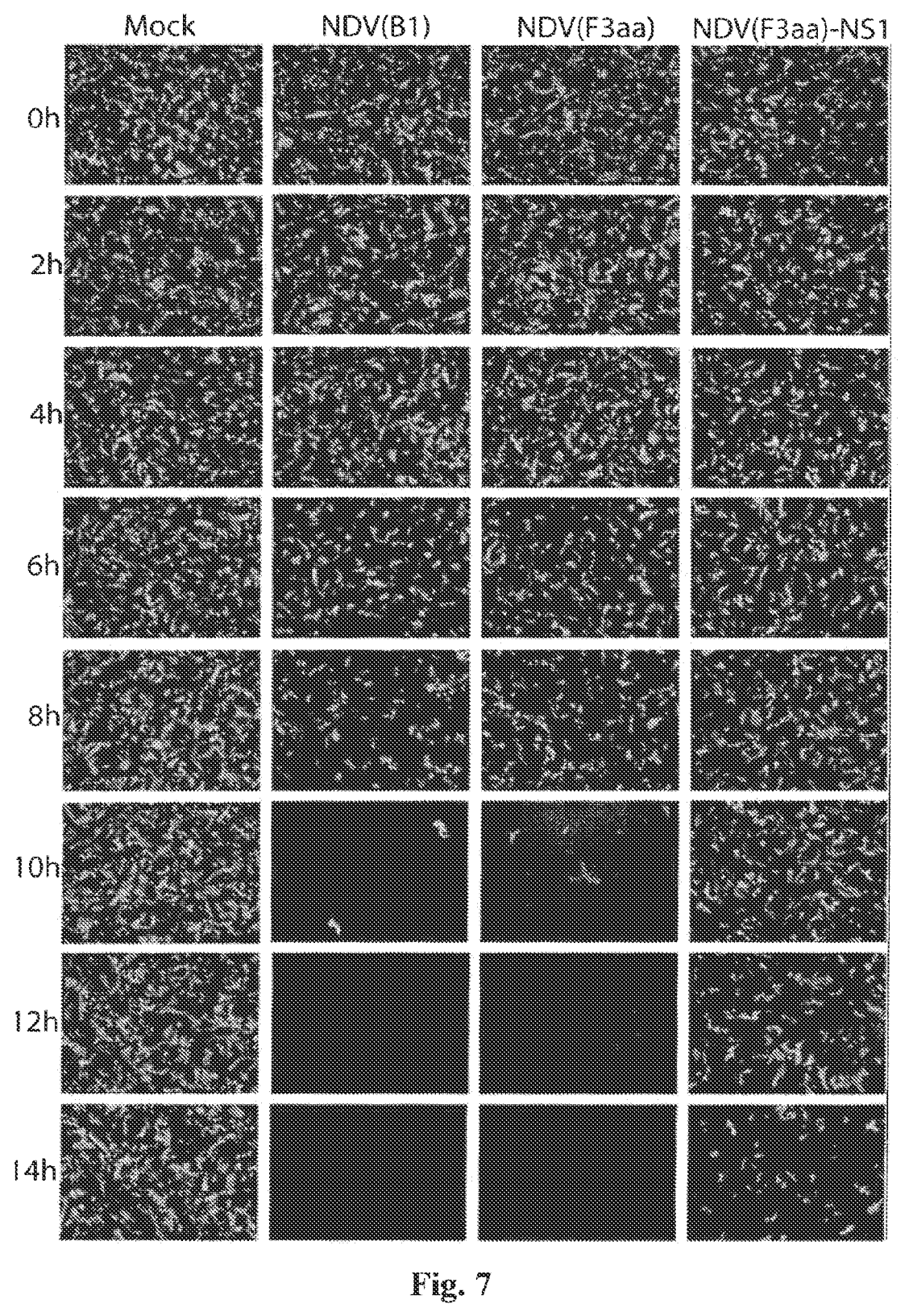

FIG. 7. Genetically engineered NDV(F3aa)-NS1 suppresses the induction of antiviral state in the infected cells. IFN induction assay was performed in HFF-1 cells, as described in FIG. 2. HFF-1 were infected with NDV(B1), NDV(F3aa), NDV(F3aa)-NS1 viruses, or were mock-infected. Infection supernatants were collected post-infection at 2 hour intervals for 14 hours and were UV-inactivated. The supernatants were then used to treat Vero cells for 6 hours, which were subsequently infected with NDV-GFP at MOI 0.1 for 20 hours.

FIG. 8. Replication of NDV(F3aa) and NDV(F3aa)-NS1 viruses in the interferon-deficient cell line Vero. Cells were infected at the indicated MOIs in triplicate and the virus production in the supernatant was assessed at 24, 48, and 72 hours by immunofluorescence.

5. DETAILED DESCRIPTION

5.1 Chimeric Newcastle Disease Virus

In one aspect, described herein are chimeric Newcastle disease viruses (NDVs), comprising a genome engineered to express a heterologous interferon antagonist. In a specific embodiment, a genome of a NDV is engineered to express a heterologous interferon antagonist. In other words, the NDV serves as the "backbone" that is engineered to express the heterologous interferon antagonist. Specific examples of heterologous interferon antagonists are provided below.

In another aspect, described herein are chimeric NDVs, comprising a genome engineered to express a heterologous interferon antagonist and a modified F protein. In one embodiment, a genome of a NDV is engineered to express a heterologous interferon antagonist and a modified F protein. In a specific embodiment, the chimeric NDV expressing the modified F protein is highly fusogenic and able to form syncytia. In another specific embodiment, the modified F protein is incorporated into the virion. In certain embodiments, the genome of a NDV engineered to express a heterologous interferon antagonist comprises an NDV V protein encoding sequence. In other embodiments, the genome of a NDV engineered to express a heterologous interferon antagonist does not comprise an NDV V protein encoding sequence.

In one embodiment, a genome of a NDV is engineered to express a heterologous interferon antagonist and a modified F protein with a mutated cleavage site. In a specific embodiment, the NDV is engineered to express a modified F protein in which the cleavage site of the F protein is modified to produce a polybasic amino acid sequence, which allows the protein to be cleaved by intracellular proteases, which makes the virus more effective in entering cells and forming syncytia. In another specific embodiment, the NDV is engineered to express a modified F protein in which the cleavage site of the F protein is replaced with one containing one or two extra arginine residues, allowing the mutant cleavage site to be activated by ubiquitously expressed proteases of the furin family. Specific examples of NDVs that express such a modified F protein include, but are not limited to, rNDV/F2aa and rNDV/F3aa. For a description of mutations introduced into a NDV F protein to produce a modified F protein with a mutated cleavage site, see, e.g., Park et al. (2006) Engineered viral vaccine constructs with dual specificity: avian influenza and Newcastle disease. *PNAS USA* 103: 8203-2808, which is incorporated herein by reference in its entirety. In certain embodiments, the modified F protein is from a different type or strain of NDV than the backbone NDV. In some embodiments, the modified F protein is in addition to the backbone NDV F protein. In specific embodiments, the modified F protein replaces the backbone NDV F protein.

In another aspect, described herein are chimeric NDVs, comprising a genome engineered to express a heterologous interferon antagonist and a tumor antigen. In a specific embodiment, a genome of a NDV is engineered to express a heterologous interferon antagonist and a tumor antigen. In certain embodiments, the genome of the NDV is engineered to express a bicistronic mRNA coding for the heterologous interferon antagonist and the tumor antigen.

In another aspect, described herein are chimeric NDVs, comprising a genome engineered to express a heterologous interferon antagonist, a modified F protein, and a tumor antigen. In a specific embodiment, the chimeric NDVs expressing the modified F protein are highly fusogenic. In a specific embodiment, a genome of a NDV is engineered to express a heterologous interferon antagonist, a tumor antigen, and a modified F protein with a mutant cleavage site (such as described herein). In specific embodiments, the modified F protein is incorporated into the virion. In certain embodiments, the genome of the NDV is engineered to express a bicistronic or multicistronic mRNA coding for one or more of the following: the heterologous interferon antagonist, the tumor antigen, and the modified F protein.

In another aspect, described herein are chimeric NDVs, comprising a genome engineered to express a heterologous interferon antagonist and a cytokine 1n one embodiment, a genome of a NDV is engineered to express a heterologous interferon antagonist and a cytokine, which are expressed and incorporated into the NDV. In certain embodiments, the genome of the NDV is engineered to express a bicistronic mRNA coding for the heterologous interferon antagonist and the cytokine Specific examples of cytokines include, but are not limited to, interleukin (IL)-2, IL-7, IL-9, IL-15, IL-22 and tumor necrosis factor (TNF)-beta. In a specific embodiment, a genome of NDV is engineered to express a heterologous interferon antagonist and IL-2.

In another aspect, described herein are chimeric NDVs, comprising a genome engineered to express a heterologous interferon antagonist, a cytokine and a modified F protein. In a specific embodiment, the chimeric NDVs expressing the modified F protein are highly fusogenic. In one embodiment, a genome of a NDV is engineered to express a heterologous interferon antagonist, a cytokine and a modified F protein with a mutant cleavage site (such as described herein). In certain embodiments, the genome of the NDV is engineered to express a bicistronic or multicistronic mRNA coding for one or more of the following: the heterologous interferon antagonist, the cytokine and the modified F protein. In a specific embodiment, a genome of NDV is engineered to express a heterologous interferon antagonist, IL-2 and a modified F protein with a mutant cleavage site (such as described herein). In specific embodiments, the modified F protein is incorporated into the virion.

In another aspect, described herein are chimeric NDVs, comprising a genome engineered to express a heterologous interferon antagonist, a cytokine and a tumor antigen. In one embodiment, a genome of a NDV is engineered to express a heterologous interferon antagonist, a cytokine and a tumor antigen. In certain embodiments, the genome of the NDV is engineered to express a bicistronic or multicistronic mRNA coding for two or more of the following: the heterologous interferon antagonist, the cytokine, and the tumor antigen. In a specific embodiment, a genome of NDV is engineered to express a heterologous interferon antagonist, IL-2 and a tumor antigen.

In another aspect, described herein are chimeric NDVs, comprising a genome engineered to express a heterologous interferon antagonist, a cytokine, a tumor antigen and a modified F protein. In a specific embodiment, the chimeric NDVs engineered to express the modified F protein are highly fusogenic. In one embodiment, a genome of a NDV is engineered to express a heterologous interferon antagonist, a cytokine, a tumor antigen and a modified F protein with a mutant cleavage site (such as described herein). In specific embodiments, the modified F protein is incorporated into the virion. In certain embodiments, the genome of the NDV is engineered to express a bicistronic or multicistronic mRNA coding for two or more of the following: the heterologous interferon antagonist, the cytokine, tumor antigen, and the modified F protein. In a specific embodiment, a genome of NDV is engineered to express a heterologous interferon antagonist, IL-2, a tumor antigen and a modified F protein with a mutant cleavage site (such as described herein).

Any NDV type or strain may serve as the backbone that is engineered to express a heterologous interferon antagonist, and in certain embodiments, engineered to express a tumor antigen, a cytokine, and/or modified F protein, including, but not limited to, naturally-occurring strains, variants or mutants, mutagenized viruses, reassortants and/or genetically engineered viruses. In a specific embodiment, the NDV that serves as the backbone for genetic engineering is a naturally-occurring strain. In certain embodiments, the NDV that serves as the backbone for genetic engineering is a lytic strain.

In other embodiments, the NDV that serves as the backbone for genetic engineering is a non-lytic strain. In certain embodiments, the NDV that serves as the backbone for genetic engineering is lentogenic strain. In some embodiments, the NDV that serves as the backbone for genetic engineering is a mesogenic strain. In other embodiments, the NDV that serves as the backbone for genetic engineering is a velogenic strain. Specific examples of NDV strains include, but are not limited to, the 73-T strain, NDV HUJ strain, Ulster strain, MTH-68 strain, Italien strain, Hickman strain, PV701 strain, Hitchner B1 strain, La Sota strain (see, e.g., Genbank No. AY845400), YG97 strain, MET95 strain, Roakin strain, and F48E9 strain. In a specific embodiment, the NDV that serves as the backbone for genetic engineering is a B1 strain as identified by Genbank No. AF309418 or NC 002617. In a specific embodiment, the NDV that serves as the backbone for genetic engineering is identified by ATCC No. VR2239. In a specific embodiment, the NDV that serves as the backbone for genetic engineering is the Hitchner B1 strain. In another specific embodiment, the NDV that serves as the backbone for genetic engineering is the La Sota strain.

In certain embodiments, attenuation, or further attenuation, of the chimeric NDV is desired such that the chimeric NDV remains, at least partially, infectious and can replicate in vivo, but only generate low titers resulting in subclinical levels of infection that are nonpathogenic (see, e.g., Khattar et al., 2009, J. Virol. 83:7779-7782). In a specific embodiment, the NDV is attenuated by deletion of the V protein. Such attenuated chimeric NDVs may be especially suited for embodiments wherein the virus is administered to a subject in order to act as an immunogen, e.g., a live vaccine. The viruses may be attenuated by any method known in the art.

In specific embodiments, in addition to expressing a heterologous interferon antagonist, and in certain embodiments, one, two or more of a tumor antigen, a modified F protein, and a cytokine, a chimeric NDV is engineered to express a suicide gene (e.g., thymidine kinase) or another molecule that inhibits NDV replication or function (a gene that makes NDV sensitive to an antibiotic or an anti-viral agent). In some embodiments, in addition to expressing a heterologous interferon antagonist, and in certain embodiments, one, two or more of a tumor antigen, a modified F protein, and a cytokine, a chimeric NDV is engineered to encode tissue-specific microRNA (miRNA) target sites (e.g., sites targeted by miR-21, miR-184, miR-133a/133b, miR-137, and/or miR-193a microRNAs).

In embodiments herein, the heterologous interferon antagonist may be inserted into the genome of the backbone NDV between two transcription units. In a specific embodiment, the heterologous interferon antagonist is inserted into the genome of the backbone NDV between the M and P transcription units or between the FIN and L transcription units. In accordance with other embodiments herein, the tumor antigen, cytokine, and/or modified F protein are inserted into the genome of the backbone NDV between two or more transcription units.

5.1.1. Interferon Antagonists

The chimeric NDVs described herein may be engineered to express any heterologous interferon antagonist known to one of skill in the art. Interferon antagonists may be identified using any technique known to one of skill in the art, including, e.g., the techniques described in U.S. Pat. Nos. 6,635,416; 7,060,430; and 7,442,527; which are incorporated herein by reference in their entirety. In a specific embodiment, the ability of a heterologous interferon antagonist to inhibit or reduce the IFN immune response in a particular subject or in cells or tissues from a particular subject is considered when selecting the heterologous interferon antagonist. For example, there may be some heterologous interferon antagonists that do not efficiently inhibit or reduce the IFN immune response (e.g., the heterologous interferon antagonist reduces the IFN immune response by less than 10% relative to a control) in a particular subject or in cells or tissues from a particular subject.

In a specific embodiment, the heterologous interferon antagonist is a viral protein. Such viral proteins may be obtained or derived from any virus and the virus may infect any species (e.g., the virus may infect humans or non-human mammals). Specific examples of such viral proteins include, but are not limited to, the influenza virus NS1 protein, Nipah virus W protein, Nipah virus V protein, Ebola virus VP35 protein, vaccinia virus E3L protein, respiratory syncytial virus (RSV) NS2, herpes simplex virus (HSV) type 1 ICP34.5 protein, and Hepatitis C NS3-4 protease. For non-limiting examples of sequences for such viral proteins, see, e.g., GenBank No. P0C1C7 (GI: 97217605) for Nipah virus W protein; GenBank No. Q99F2 (GI: 81966537) for Nipah virus V protein; GenBank No. AAG40165 (GI: 11761747), GenBank No. ACI2861 (GI:208436387), GenBank No. BAB69004 (GI: 15823610), and GenBank No. ABY75322 (GI: 165940956) for Ebola virus VP35 protein; GenBank No. AAA02759 (GI: 400554) and GenBank No. ABA82148 (GI: 77434422) for vaccinia virus E3L protein; GenBank No. AAB86657.1 (GI:2627298), GenBank No. AAC14895.1 (GI:3089373), GenBank No. AAB86669.1 (GI:2627311), GenBank No. AAC55963.1 (GI:1695256), and GenBank No. NP_048049.1 (GI:9631269) for RSV NS2 protein; GenBank No. P08353.2 (GI:585297), GenBank No. P36313.2 (GI: 189044575), and GenBank No. NP_044661.1 (GI:9629440) for type 1 ICP34.5 protein; and GenBank No. CAA47139 (GI: 505039), GenBank No. ABB90275 (GI: 83026335), GenBank No. AAF75999 (GI: 8515433), GenBank No. NP_040984.1 (GI:8486133), GenBank No. AB021703.1 (GI:126599212), and GenBank No. AAA43536.1 (GI: 324835) for influenza virus NS1. In a specific embodiment, the heterologous interferon antagonist is influenza virus NS1 protein. In another specific embodiment, the heterologous interferon antagonist is the NS1 protein from the influenza virus A/Puerto Rico/8/34 strain (known as PR8; see, e.g., GenBank No. NP_040984.1 (GI:8486133), GenBank No. AB021703.1 (GI:126599212), and GenBank No. AAA43536.1 (GI:324835)). In another specific embodiment, the heterologous interferon antagonist is influenza virus NS1 protein identified as Genbank No. ABP64726 (GI: 145322844), ABP64736 (GI:145322862), ACR15353 (GI: 237689102), ACO94842 (GI:226954813), ACO94831 (GI: 226954794), Q82506 (GI:75567388), AAA21580 (GI: 541605), ACF54603 (GI:194352380), ABF47960 (GI: 94960380), or ABF83571 (GI:107061839).

In another embodiment, the heterologous interferon antagonist is a viral protein containing one or more mutations (e.g., substitutions, deletions and/or deletions). For example, the heterologous interferon antagonist may be a mutated form of one or more of the following viral proteins: influenza virus NS1 protein, Nipah virus W protein, Nipah virus V protein, Ebola virus VP35 protein, vaccinia virus E3L protein, respiratory syncytial virus (RSV) NS2, herpes simplex virus (HSV) type 1 ICP34.5 protein, and/or Hepatitis C NS3-4 protease. In a specific embodiment, the heterologous interferon antagonist is derived from an attenuated virus. In another specific embodiment, the heterologous interferon antagonist is a viral protein that is mutated so that the ability of the viral protein to inhibit or reduce the interferon immune response is reduced by about 10%, about 15%, about 25%, about 30%, about 40%, about 50%, about 10% to about 25%, about 25% to about 50%, about 25% to about 50%, or about 25% to about 75% relative to the wild-type counterpart of the viral protein as measured by an assay known to one of skill in the art, e.g., IFN expression or the expression of a gene induced in response to IFN (such as interferon responsive gene 15 (IFRG-15)) by, e.g., an immunoassay, such as an ELISA, FACS or Western blot.

In a specific embodiment, the heterologous interferon antagonist is a mutated influenza virus NS1, wherein the mutated influenza virus NS1 is from any type of influenza virus. In a specific embodiment, the mutated influenza virus NS1 is from swine influenza virus. In a specific embodiment, the mutated influenza virus NS1 is from avian influenza virus. In a specific embodiment, the mutated influenza virus NS1 is from equine influenza virus. In a specific embodiment, the mutated influenza virus NS1 is from human influenza virus. In certain embodiments, the mutated influenza virus NS1 is from an influenza A virus. Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9. In other embodiments, the mutated influenza virus NS1 is from influenza B virus. In other embodiments, the mutated influenza virus NS1 is from influenza C virus.

In another specific embodiment, the heterologous interferon antagonist is a mutated influenza virus NS1 protein described in U.S. Pat. No. 6,669,943 or U.S. Publication Nos. 2008/0254060 (now issued as U.S. Pat. No. 7,588,768) or 2009/0010962, which are incorporated herein by reference in their entirety. In another specific embodiment, the heterologous interferon antagonist is a mutated NS1 protein of 60 to 130, 70 to 130, 70 to 126, 70 to 124, 70 to 120, 70 to 110, 70 to 100, 70 to 85, or 70 to 80 amino acids in length from the amino-terminus. In another specific embodiment, the heterologous interferon antagonist is a mutated NS1 protein of 60, 65, 70, 75, 80, 85, 90, 95, 99, 100, 105, 110, 115, 120, 124, 125, 126, 127 or 130 amino acids in length from the amino-terminus. In another specific embodiment, the heterologous interferon antagonist is a mutated NS1 protein of 60-70, 70-80, 80-90, 90-100, 100-110, 110-120, 120-130, 120-140, or 60-140 amino acids in length from the amino-terminus. In certain embodiments, the NS1 protein is counted based on the NS1 protein of the influenza virus PR8 strain (e.g., Genbank No. ABP64726 (GI:145322844), ABP64736 (GI:

145322862), ACR15353 (GI:237689102), ACO94842 (GI: 226954813), or ACO94831 (GI:226954794)) or WSN strain (e.g., Genbank No. AAA21580 (GI:541605), ACF54603 (GI: 194352380), ABF47960 (GI:94960380), or ABF83571 (GI: 107061839)).

In another specific embodiment, the heterologous interferon antagonist is a cellular protein. Such cellular proteins include, but are not limited to, dominant-negative cellular proteins that block the induction or response to innate immunity and cellular regulators of the innate immune response. Specific examples of dominant negative cellular proteins include, but are not limited to, dominant-negative STAT1 (Walter et al. (1997). Targeted inhibition of Interferon-γ-dependent intercellular adhesion molecule-1 (ICAM-1) expression using dominant-negative Stat1. *J. Biol. Chem.* 272: 28582-28589); dominant-negative RIG-1 (Yoneyama et al. (2004). The RNA helicase RIG-I has an essential function in double-stranded RNA-induced innate antiviral responses. *Nature Immunology* 5: 730-737); dominant-negative IRF-3 (Foy et al. (2003). Regulation of Interferon Regulatory Factor-3 by the Hepatitis C Virus Serine Protease. *Science:* 300: 1145-1148); dominant-negative IKK and TBK proteins (Sharma et al. (2003). Triggering the Interferon Antiviral Response Through an IKK-Related Pathway. Science 300: 1148-1151); and dominant-negative MyD88 (Dupraz et al. (2000). Dominant Negative MyD88 Proteins Inhibit Interleukin-1/Interferon—mediated Induction of Nuclear Factor B-dependent Nitrite Production and Apoptosis in Cells. *J. Biol. Chem.* 275: 37672-37678). Specific examples of cellular regulators of the innate immune response include, but are not limited to: SOCS proteins, PIAS proteins, CYLD proteins, IkB protein, Atg5 protein, Pin1 protein, IRAK-M protein, and UBP43.

5.1.2. Tumor Antigens

The chimeric NDVs described herein may be engineered to express any tumor antigen known in the art. Tumor antigens include tumor-associated antigens and tumor-specific antigens. Specific examples of tumor antigens include, but are not limited to, MAGE-1, MAGE-3, BAGE, GAGE-1, GAGE-2, N-acetylglucosaminyltransferase-V, p-15, gp100, MART-1/MelanA, TRP-1 (gp75), Tyrosinase, cyclin-dependent kinase 4, β-catenin, MUM-1, CDK4, HER-2/neu, human papillomavirus-E6, human papillomavirus E7, CD20, carcinoembryonic antigen (CEA), epidermal growth factor receptor, MUC-1, caspase-8, CD5, mucin-1, Lewisx, CA-125, p185HER2, IL-2R, Fap-α, tenascin, antigens associated with a metalloproteinase, and CAMPATH-1. Other examples include, but are not limited to, KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, CEA, polymorphic epithelial mucin antigen, milk fat globule antigen, colorectal tumor-associated antigens (such as: CEA, TAG-72, CO17-1A, GICA 19-9, CTA-1 and LEA), Burkitt's lymphoma antigen-38.13, CD19, B-lymphoma antigen-CD20, CD33, melanoma specific antigens (such as ganglioside GD2, ganglioside GD3, ganglioside GM2, ganglioside GM3), tumor-specific transplantation type of cell-surface antigen (TSTA) (such as virally-induced tumor antigens including T-antigen DNA tumor viruses and Envelope antigens of RNA tumor viruses), oncofetal antigen-alpha-fetoprotein such as CEA of colon, bladder tumor oncofetal antigen, differentiation antigen (such as human lung carcinoma antigen L6 and L20), antigens of fibrosarcoma, leukemia T cell antigen-Gp37, neoglycoprotein, sphingolipids, breast cancer antigens (such as EGFR (Epidermal growth factor receptor), HER2 antigen (p185.sup.HER2) and HER2 neu epitope), polymorphic epithelial mucin (PEM), malignant human lymphocyte antigen-APO-1, differentiation antigen (such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, D.sub.156-22 found in colorectal cancer, TRA-1-85 (blood group H), C14 found in colonic adenocarcinoma, F3 found in lung adenocarcinoma, AH6 found in gastric cancer, Y hapten, Le.sup.y found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group $Le^a$) found in Adenocarcinoma, NS-10 found in adenocarcinomas, CO-43 (blood group $Le^b$), G49 found in EGF receptor of A431 cells, MH2 (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos), T cell receptor derived peptide from a Cutaneous T cell Lymphoma, C-reactive protein (CRP), cancer antigen-50 (CA-50), cancer antigen 15-3 (CA15-3) associated with breast cancer, cancer antigen-19 (CA-19) and cancer antigen-242 associated with gastrointestinal cancers, carcinoma associated antigen (CAA), chromogranin A, epithelial mucin antigen (MC5), human epithelium specific antigen (E1A), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM.

5.2 Construction of Chimeric NDVS

The chimeric NDVs described herein can be generated using the reverse genetics technique. The reverse genetics technique involves the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in U.S. Pat. No. 6,146,642 issued Nov. 14, 2000; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper-free plasmid technology can also be utilized to engineer a chimeric NDV described herein. Briefly, a complete cDNA of a NDV (e.g., the Hitchner B1 strain) is constructed, inserted into a plasmid vector and engineered to contain a unique restriction site between two transcription units (e.g., the NDV P and M genes; or the NDV FIN and L genes). A heterologous interferon antagonist or tumor antigen may be inserted into the viral genome at the unique restriction site. Alternatively, a heterologous interferon antagonist or tumor antigen may be engineered into a NDV transcription unit so long as the insertion does not affect the ability of the virus to infect and replicate. The single segment is positioned between a T7 promoter and the hepatitis delta virus ribozyme to produce an exact negative transcript from the T7 polymerase. The plasmid vector and expression vectors comprising the necessary viral proteins are transfected into cells leading to production of recombinant viral particles (see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety).

Bicistronic techniques to produce multiple proteins from a single mRNA are known to one of skill in the art. Bicistronic techniques allow the engineering of coding sequences of multiple proteins into a single mRNA through the use of IRES sequences. IRES sequences direct the internal recruitment of ribozomes to the RNA molecule and allow downstream translation in a cap independent manner. Briefly, a coding region of one protein is inserted into the ORF of a second protein. The insertion is flanked by an IRES and any untranslated signal sequences necessary for proper expression and/or function. The insertion must not disrupt the open reading frame, polyadenylation or transcriptional promoters of the second protein (see e.g., Garcia-Sastre et al., 1994, J. Virol. 68:6254-6261 and Garcia-Sastre et al., 1994 Dev. Biol. Stand. 82:237-246, each of which are incorporated by reference herein in their entirety).

5.3 Propagation of Chimeric NDVS

The chimeric NDVs described herein can be propagated in any substrate that allows the virus to grow to titers that permit the uses of the viruses described herein. In one embodiment, the substrate allows the chimeric NDVs described herein to grow to titers comparable to those determined for the corresponding wild-type viruses.

The chimeric NDVs described herein may be grown in cells (e.g., avian cells, chicken cells, etc.) that are susceptible to infection by the viruses, embryonated eggs (e.g., chicken eggs or quail eggs) or animals (e.g., birds). Such methods are well-known to those skilled in the art. In a specific embodiment, the chimeric NDVs may be propagated in cancer cells, e.g., carcinoma cells (e.g., breast cancer cells and prostate cancer cells), sarcoma cells, leukemia cells, lymphoma cells, and germ cell tumor cells (e.g., testicular cancer cells and ovarian cancer cells). In another specific embodiment, the chimeric NDVs may be propagated in cell lines, e.g., cancer cell lines such as HeLa cells, MCF7 cells, THP-1 cells, U87 cells, DU145 cells, Lncap cells, and T47D cells. In another embodiment, the chimeric NDVs described herein are propagated in chicken cells or embryonated eggs. Representative chicken cells include, but are not limited to, chicken embryo fibroblasts and chicken embryo kidney cells. In a specific embodiment, the chimeric NDVs are propagated in Vero cells. In another specific embodiment, the chimeric NDVs are propagated in cancer cells in accordance with the methods described in Section 6, below. In another specific embodiment, the chimeric NDVs are propagated in chicken eggs or quail eggs. In certain embodiments, chimeric NDV virus is first propagated in embryonated eggs and then propagated in cells (e.g., a cell line).

The chimeric NDVs described herein may be propagated in embryonated eggs, e.g., from 6 to 14 days old. Young or immature embryonated eggs can be used to propagate the chimeric NDVs described herein. Immature embryonated eggs encompass eggs which are less than ten day old eggs, e.g., eggs 6 to 9 days old or 6 to 8 days old that are IFN-deficient. Immature embryonated eggs also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. The chimeric NDVs described herein can be propagated in different locations of the embryonated egg, e.g., the allantoic cavity. For a detailed discussion on the growth and propagation viruses, see, e.g., U.S. Pat. No. 6,852,522 and U.S. Pat. No. 7,494,808, both of which are hereby incorporated by reference in their entireties.

For virus isolation, the chimeric NDVs described herein can be removed from cell culture and separated from cellular components, typically by well known clarification procedures, e.g., such as gradient centrifugation and column chromatography, and may be further purified as desired using procedures well known to those skilled in the art, e.g., plaque assays.

5.4 Compositions & Routes of Administration

Encompassed herein is the use of a chimeric NDV described herein in compositions. Also encompassed herein is the use of plasma membrane fragments from chimeric-NDV infected cells or whole cancer cells infected with chimeric NDV in compositions. In a specific embodiment, the compositions are pharmaceutical compositions, such as immunogenic formulations (e.g., vaccine formulations). The compositions may be used in methods of treating cancer.

In one embodiment, a pharmaceutical composition comprises a chimeric NDV described herein, in an admixture with a pharmaceutically acceptable carrier. In another embodiment, a pharmaceutical composition (e.g., an oncolysate vaccine) comprises a protein concentrate or a preparation of plasma membrane fragments from chimeric NDV infected cancer cells, in an admixture with a pharmaceutically acceptable carrier. In another embodiment, a pharmaceutical composition (e.g., a whole cell vaccine) comprises cancer cells infected with chimeric NDV, in an admixture with a pharmaceutically acceptable carrier. The pharmaceutical compositions provided herein can be in any form that allows for the composition to be administered to a subject. In a specific embodiment, the pharmaceutical compositions are suitable for veterinary and/or human administration. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E.W. Martin. The formulation should suit the mode of administration.

In a specific embodiment, the pharmaceutical compositions are formulated to be suitable for the intended route of administration to a subject. For example, the pharmaceutical composition may be formulated to be suitable for parenteral, oral, intradermal, colorectal, intraperitoneal and intratumoral administration. In a specific embodiment, the pharmaceutical composition may be formulated for intravenous, oral, intraperitoneal, intranasal, intratracheal, subcutaneous, intramuscular, topical, pulmonary, or intratumoral administration.

5.5 Anti-Cancer Uses and other Uses

In one aspect, the chimeric NDVs described herein may be used in the treatment of cancer. In one embodiment, provided herein are methods for treating cancer, comprising administering to a subject in need thereof a chimeric NDV described herein or a pharmaceutical composition thereof. In a specific embodiment, provided herein is a method for treating cancer, comprising administering to a subject in need thereof an effective amount of a chimeric NDV described herein or a pharmaceutical composition thereof.

A chimeric NDV described herein or a pharmaceutical composition thereof, an oncolysate vaccine, or a whole cell cancer vaccine used in a method for treating cancer may be used as any line of therapy (e.g., a first, second, third, fourth or fifth line therapy).

In specific embodiments, a chimeric NDV engineered to express a heterologous interferon antagonist, or a pharmaceutical composition thereof is administered to a subject to treat cancer. In certain embodiments, a chimeric NDV engineered to express a heterologous interferon antagonist and a modified F protein or a pharmaceutical composition thereof is administered to a subject to treat cancer. In certain embodiments, a chimeric NDV engineered to express a heterologous interferon antagonist, a cytokine, and a modified F protein or a pharmaceutical composition thereof is administered to a subject to treat cancer. In certain embodiments, a chimeric NDV engineered to express a heterologous interferon antagonist, a tumor antigen, and a modified F protein or a pharmaceutical composition thereof is administered to a subject to treat cancer. In certain embodiments, a chimeric NDV engineered to express a heterologous interferon antagonist, a cytokine, a tumor antigen, and a modified F protein or a pharmaceutical composition thereof is administered to a subject to treat cancer. In certain embodiments, a chimeric NDV engineered to express a cytokine (e.g., IL-2), or a pharmaceutical composition thereof is administered to a subject to treat cancer. In certain embodiments, a chimeric NDV engineered to express a heterologous interferon antagonist, a microRNA, and a modified F protein or a pharmaceutical composition thereof is administered to a subject to treat cancer.

In certain embodiments, a chimeric NDV described herein is the only active ingredient administered to treat cancer. In specific embodiments, a chimeric NDV described herein is the only active ingredient in a pharmaceutical composition administered to treat cancer.

The chimeric NDV or a pharmaceutical composition thereof may be administered locally or systemically to a subject. For example, the chimeric NDV or pharmaceutical composition may be administered parenterally, intratumorally, intranasally, orally, by inhalation, topically or intradermally to a subject.

In certain embodiments, the methods described herein include the treatment of cancer for which no treatment is available. In some embodiments, a chimeric NDV described herein or a pharmaceutical composition thereof is administered to a subject to treat cancer as an alternative to other conventional therapies.

In one embodiment, provided herein is a method for treating cancer, comprising administering to a subject in need thereof a chimeric NDV described herein or a pharmaceutical composition thereof and one or more additional therapies. In a particular embodiment, one or more therapies are administered to a subject in combination with a chimeric NDV described herein or a pharmaceutical composition thereof to treat cancer. In a specific embodiment, the additional therapies are currently being used, have been used or are known to be useful in treating cancer. In another embodiment, a chimeric NDV described herein or a pharmaceutical composition thereof is administered to a subject in combination with a supportive therapy, a pain relief therapy, or other therapy that does not have a therapeutic effect on cancer. In certain embodiments, the chimeric NDV or pharmaceutical composition thereof and one or more additional therapies are administered in the same composition. In other embodiments, the chimeric NDV or pharmaceutical composition thereof and one or more additional therapies are administered in different compositions.

In certain embodiments, two, three or multiple NDVs (including one, two or more chimeric NDVs described herein) are administered to a subject to treat cancer. In specific embodiments, a first chimeric NDV engineered to express a heterologous interferon antagonist is administered to a patient to treat cancer in combination with a second chimeric NDV. The first and second chimeric NDVs may be part of the same pharmaceutical composition or different pharmaceutical compositions. In certain embodiments, the first chimeric NDV and the second chimeric NDV are administered by the same route of administration (e.g., both are administered intratumorally or intravenously). In other embodiments, the first chimeric NDV and the second chimeric NDV are administered by different routes of administration (e.g., one is administered intratumorally and the other is administered intravenously). The second or more chimeric NDVs used in accordance with methods described herein that comprise administration of two, three or multiple NDVs to a subject to treat cancer may be naturally occurring chimeric NDVs or engineered chimeric NDVs that have been engineered to express a tumor antigen, a cytokine, and/or a heterologous interferon antagonist that is not a tumor antigen or a cytokine.

In one embodiment, provided herein is a method for treating cancer, comprising administering to a subject in need thereof a first chimeric NDV and a second chimeric NDV, wherein the first chimeric NDV is engineered to express a heterologous interferon antagonist, and the second chimeric NDV is engineered to express a cytokine, such as IL-2. In a specific embodiment, the first chimeric NDV, the second chimeric NDV, or both express a modified F protein that increases the fusogenic activity of the chimeric NDV. In another specific embodiment, the first chimeric NDV, the second chimeric NDV or both express a modified F protein with a mutation in the cleavage site (such as described herein). In another embodiment, the first chimeric NDV, the second chimeric NDV or both are engineered to express a tumor antigen.

In another embodiment, provided herein is a method for treating cancer, comprising administering to a subject in need thereof a first pharmaceutical composition comprising a first chimeric NDV and a second pharmaceutical composition comprising a second chimeric NDV, wherein the first chimeric NDV is engineered to express a heterologous interferon antagonist, and the second chimeric NDV is engineered to express a cytokine, such as IL-2. In a specific embodiment, the first chimeric NDV, the second chimeric NDV, or both express a modified F protein that increases the fusogenic activity of the chimeric NDV. In another specific embodiment, the first chimeric NDV, the second chimeric NDV or both express a modified F protein with a mutation in the cleavage site (such as described herein). In another embodiment, the first chimeric NDV, the second chimeric NDV or both are engineered to express a tumor antigen.

In one embodiment, provided herein is a method for treating cancer, comprising administering to a subject in need thereof a pharmaceutical composition comprising a first chimeric NDV and a second chimeric NDV, wherein the first chimeric NDV is engineered to express a heterologous interferon antagonist, and the second chimeric NDV is engineered to express a cytokine, such as IL-2. In a specific embodiment, the first chimeric NDV, the second chimeric NDV, or both express a modified F protein that increases the fusogenic activity of the chimeric NDV. In another specific embodiment, the first chimeric NDV, the second chimeric NDV or both express a modified F protein with a mutation in the cleavage site (such as described herein). In another embodiment, the first chimeric NDV, the second chimeric NDV or both are engineered to express a tumor antigen.

In another aspect, whole cancer cells infected with a chimeric NDV described herein can be used to treat cancer. In a specific embodiment, a chimeric NDV described herein may be contacted with a cancer cell or a population of cancer cells and the infected cancer cell or population of cancer cells may be administered to a subject to treat cancer. In one embodiment, the cancer cells are subjected to gamma radiation prior to infection with a chimeric NDV described herein. In another embodiment, the cancer cells are subjected to gamma radiation after infection with a chimeric NDV described herein. In a particular embodiment, the cancer cells are treated prior to administration to a subject so that the cancer cells cannot multiply in the subject. In a specific embodiment, the cancer cells cannot multiply in the subject and the virus cannot infect the subject. In one embodiment, the cancer cells are subjected to gamma radiation prior to administration to subject. In another embodiment, the cancer cells are sonicated prior to administration to a subject. In another embodiment, the cancer cells are treated with mitomycin C prior to administration to a subject. In another embodiment, the cancer cells are treated by freezing and thawing prior to administration to a subject. In another embodiment, the cancer cells are treated with heat treatment prior to administration to a subject. The cancer cells may be administered locally or systemically to a subject. For example, the cancer cells may be administered parenterally, intratumorally, intransally, orally, by inhalation, topically or intradermally to a subject. In a specific embodiment, the cancer cells are administered intratumorally or to the skin (e.g., intradermally) of a subject. The cancer cells used may be autologous or allogeneic. In a specific embodiment, the backbone of the chimeric NDV is a non-lytic strain. The cancer cells may be administered to a subject alone or in combination with an additional therapy. The cancer cells are preferably in a pharmaceutical composition.

In another aspect, a protein concentrate or plasma membrane preparation from lysed cancer cells infected with a chimeric NDV can be used to treat cancer. In one embodiment, a plasma membrane preparation comprising fragments from cancer cells infected with a chimeric NDV described herein can be used to treat cancer. In another embodiment, a protein concentrate from cancer cells infected with a chimeric NDV described herein can be used to treat cancer. Techniques known to one of skill in the art may be used to produce the protein concentrate or plasma membrane preparation. In a specific embodiment, a chimeric NDV described herein may be contacted with a cancer cell or a population of cancer cells and the infected cancer cell or population of cancer cells may be lysed using techniques known to one of skill in the art to obtain protein concentrate or plasma membrane fragments of the NDV-infected cancer cells, and the protein concentrate or plasma membrane fragments of the NDV-infected cancer cells may be administered to a subject to treat cancer. The protein concentrate or plasma membrane fragments may be administered locally or systemically to a subject. For example, the protein concentrate or plasma membrane fragments may be administered parenterally, intratumorally, intransally, orally, by inhalation, topically or intradermally to a subject. In a specific embodiment, such a protein concentrate or plasma membrane preparation is administered intratumorally or to the skin (e.g., intradermally) of a subject. The cancer cells used to produce the protein concentrate or plasma membrane preparation may be autologous or allogeneic. In a specific embodiment, the backbone of the chimeric NDV is a lytic strain. The protein concentrate or plasma membrane preparation may be administered to a subject alone or in combination with an additional therapy. The protein concentrate or plasma membrane preparation is preferably in a pharmaceutical composition.

In another aspect, the chimeric NDVs described herein can be used to produce antibodies which can be used in diagnostic immunoassays, passive immunotherapy, and the generation of antiidiotypic antibodies. For example, a chimeric NDV described herein can be administered to a subject (e.g., a mouse, rat, pig, horse, donkey, bird or human) to generate antibodies which can then be isolated and used in diagnostic assays, passive immunotherapy and generation of antiidiotypic antibodies. The generated antibodies may be isolated by standard techniques known in the art (e.g., immunoaffinity chromatography, centrifugation, precipitation, etc.) and used in diagnostic immunoassays, passive immunotherapy and generation of antiidiotypic antibodies.

In certain embodiments, the antibodies isolated from subjects administered a chimeric NDV described herein are used to assess the expression of NDV proteins, the heterologous interferon antagonist or both. Any immunoassay system known in the art may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

5.5.1. Patient Population

In some embodiments, a chimeric NDV described herein or a pharmaceutical composition thereof, an oncolysate vaccine, or a whole cell vaccine is administered to a subject suffering from cancer. In other embodiments, a chimeric NDV described herein or a pharmaceutical composition thereof, an oncolysate vaccine, or a whole cell vaccine is administered to a subject predisposed or susceptible to cancer. In some embodiments, a chimeric NDV described herein or a pharmaceutical composition thereof, an oncolysate vaccine, or a whole cell vaccine is administered to a subject diagnosed with cancer. Specific examples of the types of cancer are described herein. In an embodiment, the subject has metastatic cancer. In another embodiment, the subject is in remission. In yet another embodiment, the subject has a recurrence of cancer.

In certain embodiments, a chimeric NDV described herein or a pharmaceutical composition thereof, an oncolysate vaccine, or a whole cell vaccine is administered to a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a chimeric NDV described herein or a pharmaceutical composition thereof, an oncolysate vaccine, or a whole cell vaccine is administered to a human infant. In other embodiments, a chimeric NDV described herein or a pharmaceutical composition thereof, an oncolysate vaccine, or a whole cell vaccine is administered to a human toddler. In other embodiments, a chimeric NDV described herein or a pharmaceutical composition thereof, an oncolysate vaccine, or a whole cell vaccine is administered to a human child. In other embodiments, a chimeric NDV described herein or a pharmaceutical composition thereof, an oncolysate vaccine, or a whole cell vaccine is administered to a human adult. In yet other embodiments, a chimeric NDV described herein or a pharmaceutical composition thereof, an oncolysate vaccine, or a whole cell vaccine is administered to an elderly human.

In certain embodiments, a chimeric NDV described herein or a pharmaceutical composition thereof, an oncolysate vaccine, or a whole cell vaccine is administered to a subject in an immunocompromised state or immunosuppressed state or at risk for becoming immunocompromised or immunosuppressed. In certain embodiments, a chimeric NDV described herein or a pharmaceutical composition thereof, an oncolysate vaccine, or a whole cell vaccine is administered to a subject receiving or recovering from immunosuppressive therapy. In certain embodiments, a chimeric NDV described herein or a pharmaceutical composition thereof, an oncolysate vaccine, or a whole cell vaccine is administered to a subject that has or is at risk of getting cancer. In certain embodiments, the subject is, will or has undergone surgery, chemotherapy and/or radiation therapy. In certain embodiments, the patient has undergone surgery to remove the tumor or neoplasm. In certain embodiments, a chimeric NDV described herein or a pharmaceutical composition thereof, an oncolysate vaccine, or a whole cell vaccine is administered to a subject that has, will have or had a tissue transplant, organ transplant or transfusion.

In some embodiments, a chimeric NDV described herein or a pharmaceutical composition thereof, an oncolysate vaccine, or a whole cell vaccine is administered to a patient who has proven refractory to therapies other than the chimeric NDV or pharmaceutical composition, but are no longer on these therapies. In a specific embodiment, a chimeric NDV described herein or a pharmaceutical composition thereof, an oncolysate vaccine, or a whole cell vaccine is administered to a patient who has proven refractory to chemotherapy. In one embodiment, that a cancer is refractory to a therapy means that at least some significant portion of the cancer cells are not killed or their cell division arrested. The determination of whether the cancer cells are refractory can be made either in vivo or in vitro by any method known in the art for assaying the effect of a therapy on cancer cells, using the art-accepted meanings of "refractory" in such a context. In a certain embodiment, refractory patient is a patient refractory to a standard therapy. In certain embodiments, a patient with cancer, is refractory to a therapy when the tumor or neoplasm has not significantly been eradicated and/or the symptoms have not been significantly alleviated. The determination of whether a patient is refractory can be made either in vivo or in vitro by any method known in the art for assaying the effectiveness of a treatment of cancer, using art-accepted meanings of "refractory" in such a context.

In certain embodiments, the patient to be treated in accordance with the methods described herein is a patient already being treated with antibiotics, anti-virals, anti-fungals, or other biological therapy/immunotherapy or anti-cancer therapy. Among these patients are refractory patients, and patients who are too young for conventional therapies. In some embodiments, the subject being administered a chimeric NDV described herein or a pharmaceutical composition thereof, an oncolysate vaccine, or a whole cell vaccine has not received therapy prior to the administration of the chimeric NDV or pharmaceutical composition, the oncolysate vaccine, or the whole cell vaccine.

In some embodiments, a chimeric NDV described herein or a pharmaceutical composition thereof, an oncolysate vaccine, or a whole cell vaccine is administered to a patient to prevent the onset of cancer in a patient at risk of developing cancer. In some embodiments, compounds are administered to a patient who are susceptible to adverse reactions to conventional therapies.

In some embodiments, the subject being administered a chimeric NDV described herein or a pharmaceutical composition thereof, an oncolysate vaccine, or a whole cell vaccine has not received prior therapy. In other embodiments, a chimeric NDV described herein or a pharmaceutical composition thereof, an oncolysate vaccine, or a whole cell vaccine is administered to a subject who has received a therapy prior to administration of the chimeric NDV or pharmaceutical composition, the oncolysate vaccine, or the whole cell vaccine. In some embodiments, the subject administered a chimeric NDV described herein or a pharmaceutical composition thereof, an oncolysate vaccine, or a whole cell vaccine experienced adverse side effects to a prior therapy or a prior therapy was discontinued due to unacceptable levels of toxicity to the subject.

5.5.2. Dosage & Frequency

The amount of a chimeric NDV or a pharmaceutical composition thereof, an oncolysate vaccine, or a whole cell vaccine which will be effective in the treatment of cancer will depend on the nature of the cancer, the route of administration, the general health of the subject, etc. and should be decided according to the judgment of a medical practitioner. Standard clinical techniques, such as in vitro assays, may optionally be employed to help identify optimal dosage ranges. However, suitable dosage ranges of chimeric NDVs for administration are generally about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu, and most preferably about $10^4$ to about $10^{12}$, and can be administered to a subject once, twice, three or more times with intervals as often as needed. Dosage ranges of oncolysate vaccines for administration may include 0.001 mg, 0.005 mg, 0.01 mg, 0.05 mg. 0.1 mg. 0.5 mg, 1.0 mg, 2.0 mg. 3.0 mg, 4.0 mg, 5.0 mg, 10.0 mg, 0.001 mg to 10.0 mg, 0.01 mg to 1.0 mg, 0.1 mg to 1 mg, and 0.1 mg to 5.0 mg, and can be administered to a subject once, twice, three or more times with intervals as often as needed. Dosage ranges of whole cell vaccines for administration may include $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ cells, and can be administered to a subject once, twice, three or more times with intervals as often as needed. In certain embodiments, dosages similar to those currently being used in clinical trials for NDV, oncolysate vaccines or whole cell vaccines are administered to a subject. Effective doses may be extrapolated from dose response curves derived from in vitro or animal model test systems.

In certain embodiments, a chimeric NDV or a pharmaceutical composition thereof is administered to a subject as a single dose followed by a second dose 3 to 6 weeks later. In accordance with these embodiments, booster inoculations may be administered to the subject at 6 to 12 month intervals following the second inoculation. In certain embodiments, an oncolysate vaccine or a whole cell vaccine is administered to a subject as a single dose followed by a second dose 3 to 6 weeks later. In one embodiment, the subject is a mammal. In a specific embodiment, the subject is a human.

In certain embodiments, administration of the same chimeric NDV or a pharmaceutical composition thereof, oncolysate vaccine, or whole cell vaccine may be repeated and the administrations may be separated by at least 1 day, 2 days, 3 days, 5 days, 10 days, 15 days, 21 days, 28 days, 30 days, 45 days, 2 months, 75 days, 3 months, or at least 6 months. In other embodiments, administration of the same chimeric NDV or a pharmaceutical composition thereof, oncolysate vaccine, or whole cell vaccine may be repeated and the administrations may be separated by 1 to 30 days, 15 to 30 days, 15 to 45 days, 15 to 75 days, 15 to 90 days, 1 to 3 months, 3 to 6 months, 3 to 12 months, or 6 to 12 months. In some embodiments, a first chimeric NDV or a pharmaceutical composition thereof is administered to a subject followed by the administration of a second chimeric NDV or a pharmaceutical composition thereof. In certain embodiments, the first and second chimeric NDVs or pharmaceutical compositions thereof may be separated by at least 1 day, 2 days, 3 days, 5 days, 10 days, 15 days, 21 days, 28 days, 30 days, 45 days, 2 months, 75 days, 3 months, or at least 6 months. In other embodiments, the first and second chimeric NDVs or pharmaceutical compositions thereof may be separated by 1 to 30 days, 15 to 30 days, 15 to 45 days, 15 to 75 days, 15 to 90 days, 1 to 3 months, 3 to 6 months, 3 to 12 months, or 6 to 12 months.

5.5.3. Types of Cancer

Specific examples of cancers that can be treated in accordance with the methods described herein include, but are not limited to: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, glioblastoma multiforme, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-cancer cell lung cancer, squamous cell carcinoma (epidermoid carcinoma), adenocarcinoma, large-cell carcinoma and cancer-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In a specific embodiment, the chimeric NDVs described herein or pharmaceutical compositions thereof, an oncolysate vaccine, or a whole cell vaccine are useful in the treatment of a variety of cancers and abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma.

In some embodiments, cancers associated with aberrations in apoptosis are treated in accordance with the methods described herein. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are treated in accordance with the methods described herein. In other specific embodiments, a sarcoma or melanoma is treated in accordance with the methods described herein.

In a specific embodiment, the cancer being treated in accordance with the methods described herein is leukemia, lymphoma or myeloma (e.g., multiple myeloma). Specific examples of leukemias and other blood-borne cancers that can be treated in accordance with the methods described herein include, but are not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", and hairy cell leukemia.

Specific examples of lymphomas that can be treated in accordance with the methods described herein include, but are not limited to, Hodgkin's disease, non-Hodgkin's Lymphoma, Multiple myeloma, Waldenström's macroglobulinemia, Heavy chain disease, and Polycythemia vera.

In another embodiment, the cancer being treated in accordance with the methods described herein is a solid tumor. Examples of solid tumors that can be treated in accordance with the methods described herein include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, cancer cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. In another embodiment, the cancer being treated in accordance with the methods described herein is a metastatic. In another embodiment, the cancer being treated in accordance with the methods described herein is malignant.

In a specific embodiment, the cancer being treated in accordance with the methods described herein is a cancer that has a poor prognosis and/or has a poor response to conventional therapies, such as chemotherapy and radiation. In another specific embodiment, the cancer being treated in accordance with the methods described herein is malignant melanoma, malignant glioma, renal cell carcinoma, pancreatic adenocarcinoma, malignant pleural mesothelioma, lung adenocarcinoma, lung small cell carcinoma, lung squamous cell carcinoma, anaplastic thyroid cancer, and head and neck squamous cell carcinoma.

5.5.4. Additional Therapies

Additional therapies that can be used in a combination with a chimeric NDV described herein or a pharmaceutical composition thereof, an oncolysate vaccine, or a whole cell vaccine for the treatment of cancer include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. In a specific embodiment, the additional therapy is a chemotherapeutic agent.

In some embodiments, a chimeric NDV described herein or a pharmaceutical composition thereof, an oncolysate vaccine, or a whole cell vaccine is used in combination with radiation therapy comprising the use of x-rays, gamma rays and other sources of radiation to destroy cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer cells and/or a tumor mass.

Currently available cancer therapies and their dosages, routes of administration and recommended usage are known in the art and have been described in such literature as the Physician's Desk Reference (63th ed., 2009).

Specific examples of anti-cancer agents that may be used in combination with a chimeric NDV described herein or a pharmaceutical composition thereof include: hormonal agents (e.g., aromatase inhibitor, selective estrogen receptor modulator (SERM), and estrogen receptor antagonist), chemotherapeutic agents (e.g., microtubule disassembly blocker, antimetabolite, topoisomerase inhibitor, and DNA crosslinker or damaging agent), anti-angiogenic agents (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with a chimeric NDV described herein or a pharmaceutical composition thereof include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with a chimeric NDV described herein or a pharmaceutical composition thereof include microtubule disassembly blocker, antimetabolite, topoisomerase inhibitor, and DNA crosslinker or damaging agent. Chemotherapeutic agents that are microtubule disassembly blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate antimetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capecitabine, gemcitabine (GEMZAR), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

5.6 Biological Assays

In Vitro Viral Assays

Viral assays include those that measure altered viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Growth of the chimeric NDVs described herein can be assessed by any method known in the art or described herein (e.g., in cell culture (e.g., cultures of chicken embryonic kidney cells or cultures of chicken embryonic fibroblasts (CEF)). Viral titer may be determined by inoculating serial dilutions of a chimeric NDV described herein into cell cultures (e.g., CEF, MDCK, EFK-2 cells, Vero cells, primary human umbilical vein endothelial cells (HUVEC), H292 human epithelial cell line or HeLa cells), chick embryos, or live animals (e.g., avians). After incubation of the virus for a specified time, the virus is isolated using standard methods. Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50). An exemplary method of assessing viral titer is described in Section 6, below.

Incorporation of the viral interferon antagonist, cytokine, tumor antigen or mutated F protein into the virion of the chimeric NDVs described herein can be assessed by any method known in the art or described herein (e.g., in cell culture, an animal model or viral culture in embryonated eggs). For example, viral particles from cell culture of the allantoic fluid of embryonated eggs can be purified by centrifugation through a sucrose cushion and subsequently analyzed for fusion protein expression by Western blotting using methods well known in the art.

Immunofluorescence-based approaches may also be used to detect virus and assess viral growth. Such approaches are well known to those of skill in the art, e.g., fluorescence microscopy and flow cytometry (see Section 6, below).

Antibody Assays

Antibodies generated by the chimeric NDVs described herein may be characterized in a variety of ways well-known to one of skill in the art (e.g., ELISA, Surface Plasmon resonance display (BIAcore), Western blot, immunofluorescence, immunostaining and/or microneutralization assays). In particular, antibodies generated by the chimeric NDVs described herein may be assayed for the ability to specifically bind to an antigen of the virus or a tumor antigen. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Antibodies generated by the chimeric NDVs described herein that have been identified to specifically bind to an antigen of the virus, a tumor antigen or a cytokine can be assayed for their specificity to said antigen of the virus, tumor antigen, or cytokine The antibodies may be assayed for specific binding to an antigen of the virus or a tumor antigen and for their cross-reactivity with other antigens by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an antigen and the off-rate of an antibody-antigen interaction can be determined by competitive binding assays. Alternatively, a surface plasmon resonance assay (e.g., BIAcore kinetic analysis) or KinExA assay (Blake, et al., Analytical Biochem., 1999, 272: 123-134) may be used to determine the binding on and off rates of antibodies to an antigen of the chimeric NDVs described herein.

IFN Assays

IFN induction and release by a chimeric NDV described herein may be determined using techniques known to one of skill in the art or described herein. For example, the amount of IFN induced in cells following infection with a chimeric NDV described herein may be determined using an immunoassay (e.g., an ELISA or Western blot assay) to measure IFN expression or to measure the expression of a protein whose expression is induced by IFN. Alternatively, the amount of IFN induced may be measured at the RNA level by assays, such as Northern blots and quantitative RT-PCR, known to one of skill in the art. In specific embodiments, the amount of IFN released may be measured using an ELISPOT assay. (See, e.g., the methods described in Section 6, below.)

Toxicity Studies

In some embodiments, the chimeric NDVs described herein or pharmaceutical compositions thereof, oncolysate vaccines, or whole cell vaccines are tested for cytotoxicity in mammalian, preferably human, cell lines (see, e.g., the cytotoxicity assay described in Section 6, below). In certain embodiments, cytotoxicity is assessed in one or more of the following non-limiting examples of cell lines: U937, a human monocyte cell line; primary peripheral blood mononuclear cells (PBMC); Huh7, a human hepatoblastoma cell line; HL60 cells, HT1080, HEK 293T and 293H, MLPC cells, human embryonic kidney cell lines; human melanoma cell lines, such as SkMel2, SkMel-119 and SkMel-197; THP-1, monocytic cells; a HeLa cell line; and neuroblastoma cells lines, such as MC-IXC, SK-N-MC, SK-N-MC, SK-N-DZ, SH-SY5Y, and BE(2)-C. In certain embodiments, cytotoxicity is assessed in various cancer cells. In some embodiments, the ToxLite assay is used to assess cytotoxicity.

Many assays well-known in the art can be used to assess viability of cells or cell lines following infection with a chimeric NDV described herein or pharmaceutical compositions thereof, oncolysate vaccines, or whole cell vaccines and, thus, determine the cytotoxicity of the chimeric NDV or pharmaceutical compositions thereof, oncolysate vaccine, or whole cell vaccine. For example, cell proliferation can be assayed by measuring Bromodeoxyuridine (BrdU) incorporation, ($^3$H) thymidine incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability. In preferred embodiments, a chimeric NDV described herein or pharmaceutical composition thereof kills cancer cells but does not kill healthy (i.e., non-cancerous) cells. In one embodiment, a chimeric NDV described herein or pharmaceutical composition thereof preferentially kills cancer cells but does not kill healthy (i.e., non-cancerous) cells.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes.

The chimeric NDVs described herein or pharmaceutical compositions thereof, oncolysate vaccines, or whole cell vaccines can be tested for in vivo toxicity in animal models (see, e.g., the animal models described in Section 6, below). For example, animal models, described herein and/or others known in the art, used to test the effects of compounds on cancer can also be used to determine the in vivo toxicity of the chimeric NDVs described herein or pharmaceutical compositions thereof, oncolysate vaccine, or whole cell vaccine. For example, animals are administered a range of pfu of a chimeric NDV described herein. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a chimeric NDV described herein or a pharmaceutical composition thereof, oncolysate vaccine, or whole cell vaccine can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibits large therapeutic indices is preferred. While therapies that exhibits toxic side effects may be used, care should be taken to design a delivery system that targets such therapies to the site of affected tissue in order to minimize potential damage to noncancerous cells and, thereby, reduce side effects.

The data obtained from the cell culture assays and animal studies can be used in formulating a range of dosage of the therapies for use in subjects. The dosage of such agents lies preferably within a range of circulating concentrations that include the ED50 with little or no toxicity. The dosage may vary within this range depending upon the dosage form employed and the route of administration utilized. For any therapy described herein, the therapeutically effective dose can be estimated initially from cell culture assays. A dose may be formulated in animal models to achieve a circulating plasma concentration range that includes the IC50 (i.e., the concentration of the chimeric NDV that achieves a half-maximal inhibition of symptoms) as determined in cell culture. Such information can be used to more accurately determine useful doses in subjects. Levels in plasma may be measured, for example, by high performance liquid chromatography.

Anti-Cancer Studies

The chimeric NDVs described herein or pharmaceutical compositions thereof, oncolysate vaccines, or whole cell vaccines can be tested for biological activity using animal models for cancer. Such animal model systems include, but are not limited to, rats, mice, chicken, cows, monkeys, pigs, dogs, rabbits, etc. In a specific embodiment, the anti-cancer activity of a chimeric NDV described herein is tested in a mouse model system. Such model systems are widely used and well-known to the skilled artisan such as the SCID mouse model or transgenic mice.

The anti-cancer activity of a chimeric NDV described herein or a pharmaceutical composition thereof, oncolysate vaccine, or whole cell vaccine can be determined by administering the chimeric NDV or pharmaceutical composition thereof, oncolysate vaccine or whole cell vaccine to an animal model and verifying that the chimeric NDV or pharmaceutical composition thereof, oncolysate vaccine or whole cell vaccine is effective in reducing the severity of cancer, reducing the symptoms of cancer, reducing cancer metastasis, and/or reducing the size of a tumor in said animal model (see, e.g., Section 6, below). Examples of animal models for cancer in general include, include, but are not limited to, spontaneously occurring tumors of companion animals (see, e.g., Vail & MacEwen, 2000, Cancer Invest 18(8):781-92). Examples of animal models for lung cancer include, but are not limited to, lung cancer animal models described by Zhang & Roth (1994, In-vivo 8(5):755-69) and a transgenic mouse model with disrupted p53 function (see, e.g. Morris et al., 1998, J La State Med Soc 150(4): 179-85). An example of an animal model for breast cancer includes, but is not limited to, a transgenic mouse that over expresses cyclin D1 (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res. 61(6):2395-8). Examples of animal models for pancreatic cancer include, but are not limited to, a metastatic model of PancO2 murine pancreatic adenocarcinoma (see, e.g., Wang et al., 2001, Int. J. Pancreatol. 29(1):37-46) and nu-nu mice generated in subcutaneous pancreatic tumors (see, e.g., Ghaneh et al., 2001, Gene Ther. 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc. Natl. Acad. Sci. USA 95(23):13853-8). An example of an animal model for esophageal cancer includes, but is not limited to, a mouse transgenic for the human papillomavirus type 16 E7 oncogene (see, e.g., Herber et al., 1996, J. Virol. 70(3): 1873-81). Examples of animal models for colorectal carcinomas include, but are not limited to, Apc mouse models (see, e.g., Fodde & Smits, 2001, Trends Mol Med 7(8):369 73 and Kuraguchi et al., 2000).

6. EXAMPLE

This example demonstrates the therapeutic efficacy of a chimeric NDV engineered to express a heterologous interferon antagonist in the treatment of cancer.

6.1 Materials & Methods

Cell Lines, Antibodies, and other Reagents

Human melanoma cell lines SkMel-2, SkMel-119, and SkMel-197 cells were maintained in RPMI medium supplemented with penicillin, streptomycin, and 10% fetal calf serum. Hep-2, A549, B16-F10 and Panc-1 cells were maintained in high-glucose DMEM medium supplemented with 10% fetal calf serum, penicillin, and streptomycin. HFF-1, SCC-15, SCC-25 and Vero cells were maintained in MEM supplemented with 10% FCS, penicillin, and streptomycin. Rabbit polyclonal serum to NDV virus and mouse monoclonal anti-NS1 antibody were described previously (Park et al. (2003). Newcastle disease virus V protein is a determinant of host range restriction. *Journal of Virology* 77: 9522-9532; Wang, et al. (2000). Influenza A virus NS1 protein prevents activation of NF-kappaB and induction of alpha/beta interferon. *Journal of Virology* 74: 11566-11573). Antibody to β-actin was from Sigma. Fluorochrome-conjugated secondary anti-mouse and anti-rabbit antibodies for microscopy were from Molecular Probes. Conjugated anti-CD4 and anti-CD8 antibodies for flow cytometry were purchased from BD Pharmingen. Cytotox LDH release assay kits were purchased from Promega. Interferon beta ELISA kits were purchased from PBL.

Virus Cloning and Rescue

The NDV mutant viruses with modified F cleavage site (NDV(F3aa)) were previously described (Park et al. (2006). Engineered viral vaccine constructs with dual specificity: avian influenza and Newcastle disease. *Proc Natl Acad Sci USA* 103: 8203-8208). To generate NDV(F3aa) virus expressing NS1, a DNA fragment encoding the influenza A/PR/8/34 NS1 protein flanked by the appropriate NDV-specific RNA transcriptional signals was inserted into the XbaI site created between the P and M genes of pT7NDV/F3aa. Viruses were rescued from cDNA using methods described previously (Nakaya et al. (2001). Recombinant Newcastle disease virus as a vaccine vector. *Journal of Virology* 75: 11868-11873) and sequenced by reverse transcription-PCR for insert fidelity.

Interferon Induction Bioassay and ELISA

To determine the amount of IFN produced in cells infected with the different recombinant NDV viruses, a bioassay described previously (Quinlivan et al. (2005). Attenuation of equine influenza viruses through truncations of the NS1 protein. *Journal of Virology* 79: 8431-8439) was modified. Briefly, human foreskin fibroblasts (HFF-1) or Panc-1 cells were infected in 6-well dishes with the viruses of interest at MOI 0.1. Infection supernatants were collected at different time points post-infection. The virus present in supernatants was inactivated in Stratalinker 1800 (Stratagene) with 6 pulses of 300 mJ/cm2 UV light. Inactivated supernatants were then serially diluted and used to treat Vero cells in 96-well plates for 6 hours. Supernatants from uninfected cells and human IFN beta (R and D systems) were used as negative and positive controls, respectively. Vero cells were subsequently washed and infected with NDV(B1)-GFP virus at MOI 0.1 for 20 hours. At 20 hours post-infection, the cells were examined for GFP expression under fluorescent microscope. Presence of antiviral cytokines in the supernatant induces an antiviral state in Vero cells, which prevents subsequent infection with NDV(B1)-GFP. In this assay, the amount of IFN is inversely proportional to the amount of GFP expression. IFNβ secretion was further measured by ELISA, according to the manufacturer's instructions (PBL).

LDH Release Assays

Cells were infected in 12-well plates for 24, 48, and 72 hours in triplicate for each condition. At each time point, the media was aspirated and the cells were washed with 1 ml of PBS. The cells were subsequently incubated with 1% Triton X-100 at 37° C. for 30 min. LDH activity in the lysates was determined using the Promega CytoTox 96 assay kit, according to the manufacturer's instructions.

Infections and Virus Titers

Cells of interest were incubated at room temperature with the virus in 12-well culture dishes at the indicated MOIs in a total volume of 100 µl. One hour after the incubation, the infection media was aspirated and the cells were incubated at 37° C. in 1 ml of DMEM with 0.3% BSA. To the cells infected with wild-type NDV(B1) virus 10% chick allantoic fluid was added to the medium to allow for fusion protein activation. After 24, 48, and 72 hours, the supernatants were collected and the virus titers were determined by serial dilution and immunofluorescence in Vero cells.

Fluorescence Microscopy

Cells were cultured on 10 mm cover slips and infected with viruses of interest at an MOI of 0.001. Twenty hours later, the cells were fixed with 5% formaldehyde in PBS and permeabilized with 1% Triton X-100. Proteins of interest were visualized by indirect immunofluorescence. Cells were probed with specific primary antibody for 2 hours at room temperature, washed, and labeled with secondary antibody conjugated to a specific fluorophore. DAPI staining was used to visualize cell nuclei. Labeled cells were visualized by laser scanning confocal microscopy (Leica TCS-SP) with TCS-SP software for image capture.

Mouse Experiments

Cultured B16-F10 cells ($1 \times 10^5$) were inoculated into the right posterior footpad of 6-8 week old C57/BL6J mice in a total volume of 50 µl. On day 7 or 10 post-inoculation, the mice were treated by intratumoral injection of $5 \times 10^6$ NDV virus of interest or PBS, in a total volume of 50 µL. The treatments were repeated every other day for a total of 4 or 6 treatments, respectively.

Tumor sizes and mouse weights were recorded every other day. According to the institutional protocols, the animals were euthanized when the tumors reached 8 mm in length. On day 25, all 8 animals from the control group and 5 animals from each treatment group were euthanized, and their spleens, popliteal lymph nodes, and tumors were collected. The remaining mice in each treatment group were observed for 120 days with measurement of tumor sizes every other day.

Splenocyte Collection, IFNγ Release and CTL Assays

Spleens were removed from the euthanized animals and splenocytes were isolated by passing the spleens through 80 µm nylon mesh filters. Cultured B16-F10 cells ($5 \times 10^5$) were treated with 50 µg/mL of mitomycin C for 2 hours at 37° C. to induce cell cycle arrest. After the treatment, the cells were washed with PBS and incubated with $1 \times 10^7$ splenocytes in RPMI with 10% FCS for 5 days. On day 3, the supernatants were collected and tested for IFNγ release by ELISA using Quantikine M kit (R&D Systems). On day 5, the splenocytes were collected, washed, counted, and co-cultured for 4 hours with $1 \times 10^3$ B16-F10 cells at the stimulator: effector ratios of 1:1.25, 1:2.5, 1:5, 1:10, 1:20, and 1:40. Specific CTL activity was determined by LDH release from the target cells utilizing the CytoTox 96 LDH kit from Promega according to the manufacturer's instructions.

Flow Cytometry

The tumors of sacrificed animals were dissected and manually dissociated with scissors. Dissociated tissue was then collected and incubated at 37° C. in 3 mL of RPMI and 50 µL of Liberase Blendzyme 3 (Roche Diagnostics). After 30 minutes of incubation, 120 µL of 0.5M EDTA were added to the cell homogenates and mixed for 5 minutes. Cells were then filtered using a cell strainer and stained with anti-CD4, and anti-CD8 antibodies (GK1.5, and 53-6.7, respectively; BD PharMingen) and flow cytomety was done in a Cytomics FC500 machine (Beckman Coulter) and analyzed using FlowJo software (Tree Star).

6.2 Results

Modification of the NDV F protein to a fusogenic type by introduction of a polybasic protease cleavage site has been shown to permit efficient formation of syncytia in the infected cells and to enhance the viral oncolytic activity of the virus in vitro and in vivo (Vigil et al. (2007). Use of reverse genetics to enhance the oncolytic properties of Newcastle disease virus. *Cancer Research* 67: 8285-8292). To explore the oncolytic potential of the fusogenic NDV, a number of tumor cell lines from a variety of cancer types, including human pancreatic, breast, thyroid, head and neck, and gastric cancers, as well as human and murine malignant melanoma cell lines, were infected with NDV(B1) and NDV(F3aa) viruses at MOI 0.1. As shown in FIG. 1, NDV was effective against the majority of tumor cell types, with NDV(F3aa) being significantly more cytolytic than the parental non-fusogenic NDV (B1) virus for the majority of cell lines. Infection of the same cell lines with NDV(F3aa) virus expressing GFP(NDV (F3aa)-GFP) revealed that the virus effectively formed large syncytia, which was likely responsible for its enhanced cytolytic activity (FIG. 1B).

Despite its effective oncolytic activity in CT26 cells both in vitro and in vivo, previous studies have shown that the NDV (F3aa) virus still failed to cause complete tumor regressions in the CT26 murine syngeneic flank tumor model (Vigil et al. (2007). Use of reverse genetics to enhance the oncolytic properties of Newcastle disease virus. *Cancer Research* 67: 8285-8292; Vigil et al. (2008). Recombinant Newcastle disease virus as a vaccine vector for cancer therapy. *Mol Ther* 16: 1883-1890). One theory to explain these results is that effective viral replication in tumors is limited by the host and tumor factors, such as the induction of type I interferon (IFN). To test whether the NDV(B1) and NDV(F3aa) induce type I IFN in NDV-susceptible human cells, an IFN bioassay, similar to the methods described previously (see Materials and Methods and FIG. 2A), was performed. As shown in FIG. 2B, infection of Panc-1 cells with NDV(B1) and NDV(F3aa) viruses led to the induction of antiviral cytokines at the levels comparable to 1000 U/ml of IFNβ, which was sufficient two suppress NDV-GFP replication. These results indicate that even in an apparently NDV-susceptible cancer cell line, the induction of type I IFN may suppress viral replication, limiting the viral oncolytic efficacy.

Repression of IFN induction during NDV infection should permit better viral replication in tumors, while maintaining the therapeutic safety margin of the virus. Using the NDV (F3aa) virus as a backbone, a virus expressing the NS1 protein of the influenza virus PR8 strain was constructed according to previously described methods (Nakaya et al. (2001). Recombinant Newcastle disease virus as a vaccine vector. *Journal of virology* 75: 11868-11873) (FIG. 3A). Immunofluorescent labeling of the infected Vero cells confirmed that the NS1 protein was expressed by the NDV(F3aa)-NS1 virus and not by the parental NDV(F3aa) or NDV(B1) strains (FIG. 3B). All of the cells infected with NDV(F3aa)-NS1 showed expression of the NS1 protein. The expression was maintained after 10 viral passages in embryonated chicken eggs, confirming the stability of the recombinant virus (data not shown). To confirm that the NS1 protein was expressed to high levels, a time course of NDV infection in Vero cells was performed and the induction of NS1 expression within the period of one viral cycle was analyzed. As shown FIG. 3C, at MOI 0.1 NS1 could be detected as early as 9 hours post-infection.

Figures 5A, 5B:
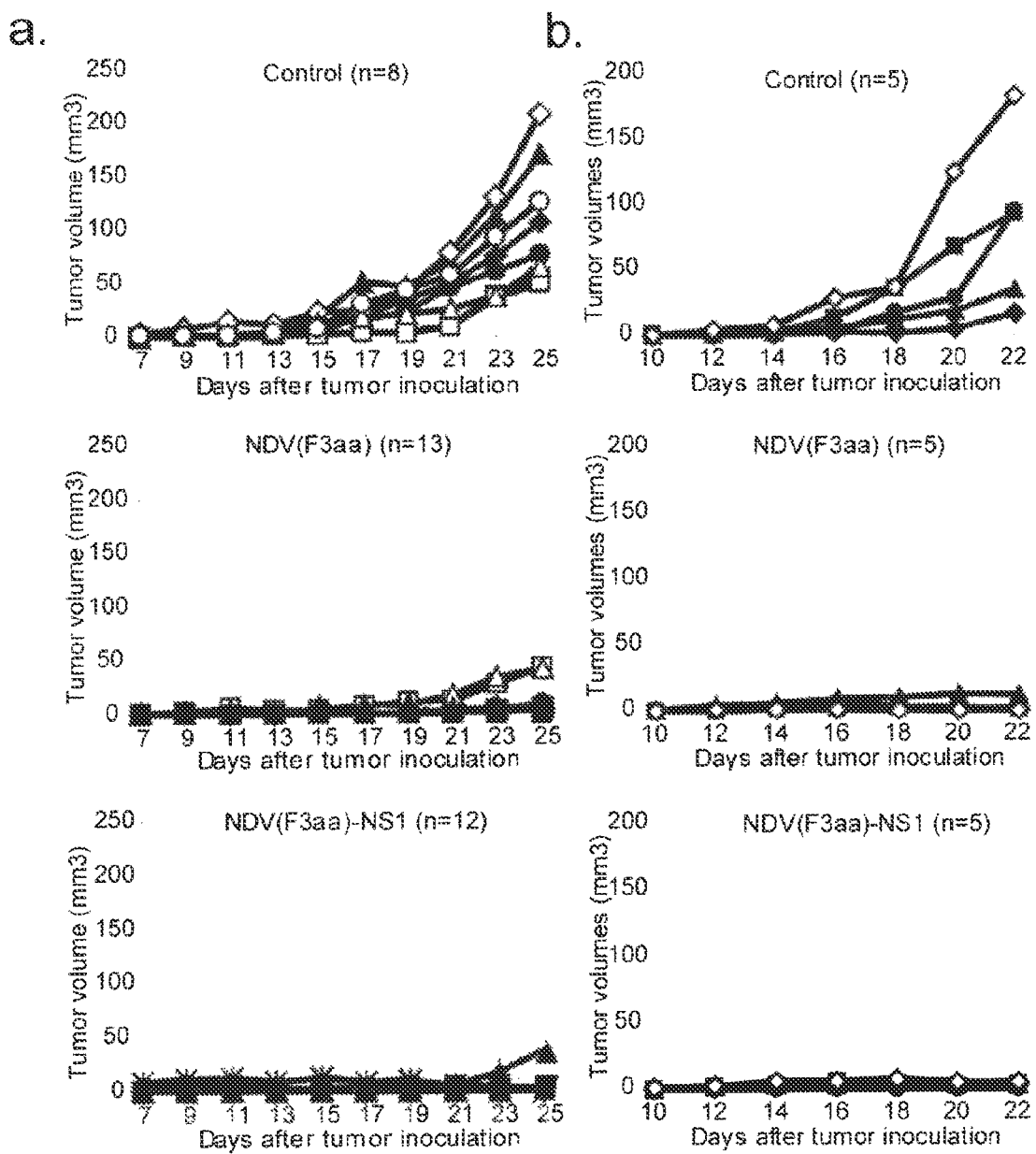

To confirm that the NS1 protein expressed within the context of the NDV genome antagonizes induction of the innate response in human cells, an IFN bioassay for the time course of IFN induction was performed (FIG. 7). To ensure that the recombinant virus is still capable of eliciting an anti-viral response in non-cancerous cells, the assay was performed in primary human foreskin fibroblasts (HFF-1) along with pancreatic cancer cell line Panc-1. Infection of HFF-1 cells with NDV(B1) and NDV(F3aa) viruses led to the induction of antiviral cytokines by 10 hours of infection (FIG. 7). By contrast, the infection with NDV(F3aa)-NS1 virus delayed the induction of antiviral cytokines by 6 hours, confirming the stronger ability of the NDV(F3aa)-NS1 virus to antagonize the induction of the innate immune response. Similar results were observed in Panc-1 cells (data not shown).

The efficiency of the NDV(F3aa)-NS1 virus in lysis of various human tumor cell lines was tested. The virus proved to be more effective than the NDV(F3aa) against the majority of cell lines tested (data not shown).

To determine the extent of the NDV replication and cytotoxicity in the melanoma cell lines, the human melanoma cell line SkMel-2, and the mouse melanoma cell line B16-F10 were selected. While all viruses exhibited significant cytolytic activity in both cell lines, NDV(F3aa) and NDV (F3aa)-NS1 were most effective (FIG. 4A). At lower MOI's, NDV(F3aa)-NS1 proved to be the most effective cytolytic agent out of all viruses in both cell lines. Similar results were observed in the SkMel-119 and SkMel-197 cell lines (data not shown).

Interestingly, both B16-F10 and SkMel-2 cells infected with the NDV(F3aa)-NS1 virus exhibited enhanced syncytia formation, when compared with the cells infected with NDV (F3aa) (FIG. 4B). At MOIs of 0.1 and 1, the majority of NDV(F3aa)-NS1-infected cells were fused into syncytia by 24 hours of infection and detached from the plate by 48 hours. Formation of syncytia without significant early cytolysis suggested that expression of NS1 by NDV protected the cells from early lysis. This finding is consistent with the known anti-apoptotic and anti-IFN properties of the influenza NS1 protein Wang et al. (2000). Influenza A virus NS1 protein prevents activation of NF-kappaB and induction of alpha/beta interferon. *Journal of Virology* 74: 11566-11573; Garcia-Sastre et al. (1998). Influenza A virus lacking the NS1 gene replicates in interferon-deficient systems. *Virology* 252: 324-330; Talon et al. (2000). Activation of interferon regulatory factor 3 is inhibited by the influenza A virus NS1 protein. *Journal of Virology* 74: 7989-7996; Bergmann et al. (2001). A genetically engineered influenza A virus with ras-dependent oncolytic properties. *Cancer Research* 61: 8188-8193; Zhirnov et al. (2002). NS1 protein of influenza A virus down-regulates apoptosis. *Journal of Virology* 76: 1617-1625; Stasakova et al. (2005). Influenza A mutant viruses with altered NS1 protein function provoke caspase-1 activation in primary human macrophages, resulting in fast apoptosis and release of high levels of interleukins 1beta and 18. *The Journal of General Virology* 86: 185-195). One theory is that these functions of the NS1 protein allowed the fused cells to survive longer, which in turn results in enhanced viral replication. Indeed, NDV(F3aa)-NS1 virus replicated to higher titers than the NDV(F3aa) virus (FIG. 4C). Interestingly, when replication of the viruses was compared in the interferon-deficient cell line Vero and embryonated chick eggs, NDV(F3aa)-NS1 replicated to similar or even lower titers than the NDV(F3aa) virus (FIG. 8 and data not shown). These data support that the enhanced cytolytic effect and replication of NDV(F3aa)-NS1 virus are dependent on its ability to antagonize mammalian interferon response.

To confirm that the NDV(F3aa)-NS1 indeed antagonizes interferon induction in melanoma cell lines, an ELISA for human and murine IFNβ secreted from the NDV-infected SkMel-2 and B16-F10 cells, respectively, was performed. As shown in FIG. 4D, IFNβ induction was delayed in NDV (F3aa)-NS1-infected cells, when compared to the NDV (F3aa)-infected controls.

Overall, these findings suggested that the NDV(F3aa)-NS1 virus was an effective cytolytic agent for the melanoma cell lines in vitro. In order to assess whether the observed in vitro cytolytic effect by NDV would translate to better anti-tumor efficacy in vivo, the syngeneic B16-F10 mouse footpad melanoma model was used. The B16-F10 cell line is known for its particularly aggressive tumor growth, early metastases, and very poor response to therapy (Poste et al. (1980). In vitro selection of murine B16 melanoma variants with enhanced tissue-invasive properties. *Cancer Research* 40: 1636-1644; Lee et al. (2006). Enhanced antitumor effect of oncolytic adenovirus expressing interleukin-12 and B7-1 in an immunocompetent murine model. *Clin Cancer Res* 12: 5859-5868; Entin et al. (2003). Tumor growth retardation, cure, and induction of antitumor immunity in B16 melanoma-bearing mice by low electric field-enhanced chemotherapy. *Clin Cancer Res* 9: 3190-3197; Rochlitz et al. (2002). Immunotherapy of metastatic melanoma by intratumoral injections of Vero cells producing human IL-2: phase II randomized study comparing two dose levels. *Cancer Gene Ther* 9: 289-295; Seliger et al. (2001). Characterization of the major histocompatibility complex class I deficiencies in B16 melanoma cells. *Cancer Res* 61: 1095-1099). Since the naturally-occurring NDV(B1) virus was previously demonstrated to be less effective in oncolysis than the fusogenic NDV(F3aa) (Vigil et al. (2007). Use of reverse genetics to enhance the oncolytic properties of Newcastle disease virus. *Cancer Research* 67: 8285-8292), and the in vitro studies showed superior efficacy of the NDV (F3aa) viruses, NDV(B1) was not used in the mouse studies.

Toxicity studies were initially performed by inoculating three (3) C57/BL6 mice subcutaneously and three (3) C57/BL6 mice intravenously with $5\times10^7$ pfu of NDV(F3aa) and NDV(F3aa)-NS1 viruses. Over the next 2 weeks, none of the animals exhibited signs of distress and continued to gain weight (data not shown). To demonstrate the efficiency of NDV(F3aa)-NS1 virus in oncolytic therapy, a low-dose treatment regimen ($5\times10^6$ pfu) extended over 4 to 6 doses was used.

For tumor studies, C57/BL6 mice from each group were inoculated into the right posterior footpad with 1×105 cultured B16-F10 cells. Tumors were allowed to develop for 7 days, at which point a pigmented tumor focus was visible in each of the animals. On day 7, the right posterior footpad of each animal was injected with 5×106 of NDV(F3aa), NDV (F3aa)-NS1, or PBS control. Eight mice were included in the control group, while 12-13 mice were used for each virus treatment group. The inoculation with $5\times10^6$ of each respective virus was repeated on days 9, 11, and 13 (4 injections total). The most common side effect was the development of localized swelling at the injection site, which subsided over the next few days after the last inoculation.

None of the animals exhibited significant weight loss over the study period (data not shown). On day 25 after tumor implantation, 8/8 control mice developed tumors of significant size and were euthanized. In addition, six animals from the NDV(F3aa) group and 5 animals from the NDV(F3aa)-NS1 group were randomly selected, sacrificed, and spleens were removed for analysis of tumor cellular immunity, while the rest of the animals continued to be followed for tumor growth (see below). As shown in FIG. 5A, on day 25 only 2/13 animals in the NDV(F3aa) group and only 1/12 animals in the NDV(F3aa)-NS1 group exhibited significantly visible tumors, which were still smaller than the majority of tumors in the control group.

To determine whether the viruses would be effective in clearing tumors at a later stage, the tumors were allowed to develop for 10 days and a total of 6 injections of each virus were used. As shown in FIG. 5B, treatment with both NDV (F3aa) and NDV(F3aa)-NS1 viruses markedly suppressed tumor growth in all animals, with only minor tumors being detectable on the day of sacrifice. These results indicate that increased number of treatments may be effective in clearing the tumors in later stages of development. The tumors were further processed for analysis for lymphocyte infiltration (see below).

Figure 5C:
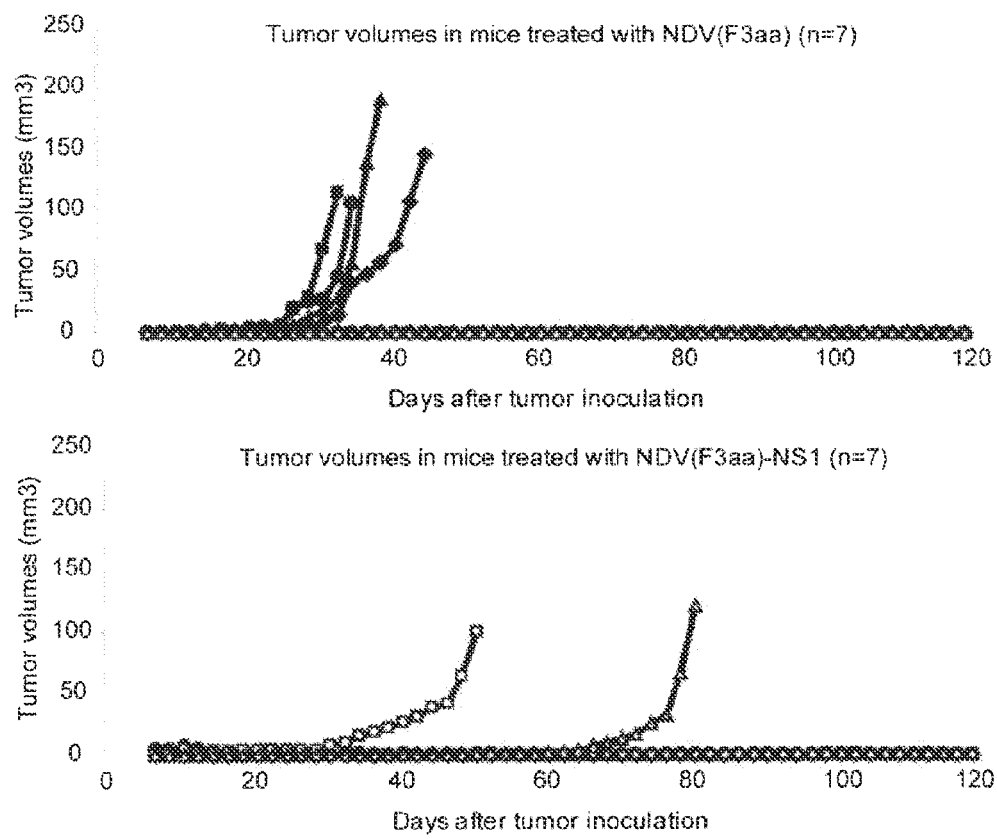
Figure 5D:
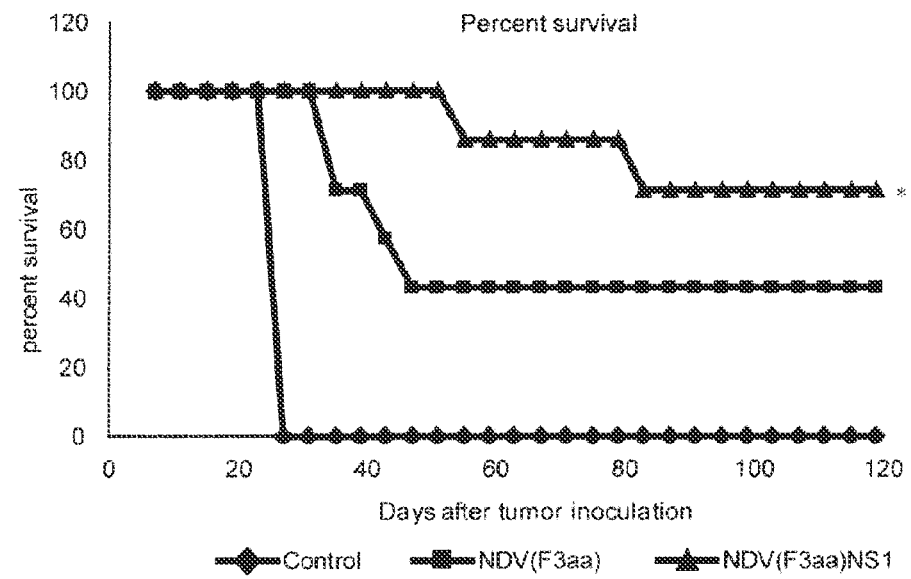

The remaining animals from the early tumor treatment group continued to be followed to determine the long-term efficacy of each viral treatment. Over the next 120 days, 4/7 animals in the NDV(F3aa) group developed significant tumors and needed to be sacrificed, while only 2/7 animals in the NDV(F3aa)-NS1 group developed tumors that required animal euthanasia (FIG. 5C). Of note, these tumors took longer to develop than those in the animals from the NDV (F3aa) group. The remaining animals in each group either completely cleared the tumor (1/3 in the NDV(F3aa) group and 1/6 in the NDV(F3aa)-NS1 group), or had a persistent pigmented focus that remained stable. The overall survival for the animals in the long-term study was 0/8 for the control group, 3/7 for the NDV(F3aa) group and 5/7 for the NDV (F3aa)-NS1 group (FIG. 5D).

The effect of virus-treated tumors on the level of immune cell infiltration was assessed. As the tumors from the early treatment group were either too small or undetectable in size for cellular fractionation, tumors from the later treatment group were used in the analysis. Tumors from the sacrificed mice described above were collected on day 22, dissected and filtered, and stained for CD4 and CD8 antigen expression. As shown in FIG. 6A, tumors from the animals treated with NDV(F3aa) and NDV(F3aa)-NS1 viruses exhibited a high degree of both CD4 and CD8 cell infiltration, suggesting the development of an immune response to the infection and/or tumor. These results also indicated that suppression of the innate immune response by the NDV(F3aa)-NS1 virus had no negative effect on the adaptive immune response to the tumor and the infection.

To determine whether the treated mice develop an adaptive immune response to melanoma cells, animals sacrificed on day 25 were assessed for the development of CTL responses against B16-F10 cells. Splenocytes from the animals were co-cultured with mitomycin C-inactivated B16-F10 cells for 5 days and assessed for IFNγ release on day 3 and for B16-F10-specific CTL activity on day 5. As shown in FIGS. 6B and 6C, treatment with both NDV(F3aa) and NDV(F3aa)-NS1 viruses resulted in enhanced IFN release and enhanced CTL activity, when compared to the control. These results suggested that tumor treatment with NDV resulted in generation of tumor-specific CTL responses, which may have contributed to the long-lasting anti-tumor effect of the virus.

6.3 Discussion

Sensitivity of NDV to the antiviral effects of IFN has been previously proposed to underlie its selective oncolytic properties (Fiola et al. (2006). Tumor selective replication of Newcastle disease virus: association with defects of tumor cells in antiviral defence. *Int J Cancer* 119: 328-338; Krishnamurthy et al. (2006). Differentially regulated interferon response determines the outcome of Newcastle disease virus infection in normal and tumor cell lines. *J. Virol.* 80: 5145-5155.). Based on these findings, the use of IFN-sensitive viruses has been suggested for oncolytic virus therapy, as many tumors have been demonstrated to be deficient in type I IFN response. Despite these findings, the use of naturally-occurring strains of NDV in human clinical trials suggested that many of the human tumors still demonstrate resistance to NDV infection (Freeman et al. (2006). Phase I/II trial of intravenous NDV-HUJ oncolytic virus in recurrent glioblastoma multiforme. *Mol. Ther.* 13: 221-228; Lorence et al. (2007). Phase 1 clinical experience using intravenous administration of PV701, an oncolytic Newcastle disease virus. *Curr Cancer Drug Targets* 7: 157-167). Studies of human tumor cell lines have shown that tumor cells are still capable of mounting antiviral responses that could limit NDV replication and its oncolytic efficacy (Geiss et al. (2002). Cellular transcriptional profiling in influenza A virus-infected lung epithelial cells: the role of the nonstructural NS1 protein in the evasion of the host innate defense and its potential contribution to pandemic influenza. *Proc Natl Acad Sci USA*. 99: 10736-10741; Haralambieva et al. (2007). Engineering oncolytic measles virus to circumvent the intracellular innate immune response. *Mol. Ther.* 15: 588-597; Vigil et al. (2007) Use of reverse genetics to enhance the oncolytic properties of Newcastle disease virus. *Cancer Res.* 67: 8285-8292).

As described herein, the reverse-genetics system for the lentogenic (avirulent) NDV Hitchner B1 strain (NDV(B1)) was used to engineer a virus with two alterations to improve the viral oncolytic properties: modification of the viral fusion protein to allow a more efficient spread between the infected cells, and introduction of an IFN-antagonist protein to attenuate the innate immune response to the infection.

Modification of the cleavage site of the NDV F protein to a polybasic amino acid sequence allows the protein to be cleaved by intracellular proteases, making the virus more effective in entering cells and forming syncytia (de Leeuw et al. (2005). Virulence of Newcastle disease virus is determined by the cleavage site of the fusion protein and by both the stem region and globular head of the haemagglutinin-neuraminidase protein. *J Gen Virol.* 86: 1759-1769; Peeters et al. (1999). Rescue of Newcastle disease virus from cloned cDNA: evidence that cleavability of the fusion protein is a major determinant for virulence. *J. Virol.* 73: 5001-5009). As demonstrated herein, a virus with a modified fusion protein (NDV(F3aa)) allowed for more efficient virus spread between tumor cells through formation of syncytia, resulted in increased viral replication, and showed enhanced oncolysis in various tumor cell lines, when compared to the wild-type NDV. Nevertheless, despite the enhanced replication and spread, the NDV(F3aa) virus still induced significant antiviral signaling in the infected tumor cells, imposing a limitation on the oncolytic efficacy of NDV in vivo.

To dampen the antiviral signaling in NDV infected cells while maintaining the nonpathogenicity of the virus in animal models, the NS1 protein of influenza A virus, which was previously shown to block the induction of antiviral signaling in influenza virus-infected cells, was introduced into the NDV with modified F protein (Garcia-Sastre et al. (1998). Influenza A virus lacking the NS1 gene replicates in interferon-deficient systems. *Virology* 252: 324-330; Mibayashi et al. (2007) Inhibition of retinoic acid-inducible gene I-mediated induction of beta interferon by the NS1 protein of influenza A virus. *J. Virol.* 81: 514-524; Wang et al. (2000). Influenza A virus NS1 protein prevents activation of NF-kappaB and induction of alpha/beta interferon. *J. Virol.* 74: 11566-11573).

Infection of human primary fibroblasts with NDV(F3aa)-NS1 virus showed that the virus was still capable of inducing a strong antiviral response in noncancerous cells, though the induction was delayed when compared to the NDV(B1) and NDV(F3aa). When compared to the NDV(F3aa) virus, NDV (F3aa)-NS1 replicated more efficiently and resulted in enhanced formation of syncytia between tumor cells. This efficacy was further demonstrated in the syngeneic B16-F10 murine melanoma model. Intratumoral treatment with NDV (F3aa)-NS1 virus led to an effective tumor arrest or regression and high percentage of animal survival. Moreover, suppression of innate responses by the NS1 protein had no major effect on the generation of adaptive immune responses to the infected tumor cells, as was demonstrated by tumor lymphocyte infiltration, and generation of tumor-specific CTL responses.

Of note, none of the animals developed side effects to the virus, suggesting that the virus is still sufficiently attenuated not to cause disease. Several factors play a role in maintenance of the observed therapeutic safety margin. First of all, while the NS1 protein enhances the ability of NDV to replicate more efficiently in mammalian cells, the loss of viral species specificity for avian cells is not absolute (see Park et al., 2003, J. Virol. 77:9522-9532). In particular, viral receptor specificity for avian cells as a result of binding of the viral FN to α2,3-linked sialogly-coproteins limits its infectivity in mammalian cells, as was shown for influenza hemagglutinin protein (see Rivetz et al., 1985, Arch. Virol. 85:231-255; and Suzuki, 2005, Biol. Pharm. Bull. 28:399-408). Second, the Hitchner B1 strain used is a lentogenic (nonpathogenic) avian strain, possessing other attenuating mutations, which likely also limit its replication in mammalian cells. Third, while the NDV(F3aa)-NS1 virus delayed the induction of IFN response in the primary human cells HFF-1, it did not completely abolish it. In fact, by 16 hours it resulted in induction of enough IFN to suppress further NDV replication.

As demonstrated, intravenous or subcutaneous injection of at least $5 \times 10^7$ pfu of NDV(F3aa) or NDV(F3aa)-NS1 resulted in no significant side effects. For the study of viral oncolytic efficacy, a tenfold lower dose ($5 \times 10^6$ pfu) per injection was used for a total of four treatments, primarily due to limitation of a solution volume that could be injected into the footpad. This dose is lower than the doses used in the majority of the previous studies using naturally occurring NDV strains (see Vigil et al., 2007, Cancer Res. 67:8285-8292; Schirrmacher et al., 2001, Int. J. Oncol. 18:945-952; and Phuangsab et al., 2001, Cancer Lett. 172:27-36). The use of higher doses and administration of longer treatment regimens could result in an even more significant oncolytic effect and survival. Indeed, treatment of B16-F10 tumors at later stages with six doses of NDV was effective in induction of tumor regressions, when compared to the untreated controls.

While the syngeneic mouse melanoma model was used herein as the primary assessment tool of the viral oncolytic efficacy, it was also shown that the NDV(F3aa)-NS1 virus is a more effective oncolytic agent in a variety of human tumor cell lines. In particular, the virus proved to be cytotoxic to all of the human malignant melanoma cell lines tested, where it replicated to significantly higher titers and formed larger syncytia than its NDV(F3aa) counterpart. These findings demonstrate the oncolytic efficacy of the virus in the in vivo models of human melanomas and other tumors.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A chimeric Newcastle disease virus (NIV), comprising a packaged genome which encodes a heterologous interferon antagonist and a modified F protein with a mutated cleavage site, wherein the heterologous interferon antagonist and the modified F protein are expressed by the virus.

2. The chimeric NDV of claim 1, wherein the heterologous interferon antagonist is an influenza virus NS1 protein.

3. The chimeric NDV of claim 1, wherein the heterologous interferon antagonist is Nipah virus W protein, Nipah V protein, Ebola virus VP35 protein, Vaccinia virus E3L, protein, respiratory syncytial virus (RSV)NS2 protein or Hepatitis C virus NS3-4 protease.

4. The chimeric NDV of claim 1, wherein the packaged genome encodes a tumor antigen, so that the tumor antigen is expressed by the virus.

5. A pharmaceutical composition comprising the chimeric NDV of claim 1 and a pharmaceutically acceptable carrier.

6. A pharmaceutical composition comprising the chinieric NDV of claim 2 and a pharmaceutically acceptable carrier.

7. The chimeric NDV of claim 1 further encoding a cytokine that is expressed by the virus.

8. The chimeric NDV of claim 7, wherein the cytokine is IL-2.

9. The chimeric NDV of claim 7, wherein the cytokine is 1L-15.

10. The chimeric NDV of claim 7, wherein the cytokine is IL-7, IL-9, IL- 22, or tumor necrosis factor-beta.

11. An isolated cell line comprising the chimeric NDV of claim 1.

12. An isolated embryonated chicken or quail egg comprising the chimeric NDV of claim 1.

13. A method for producing a pharmaceutical composition, the method comprising:
  (a) propagating the chimeric NDV of claim 1 in a cell line that is susceptible to a NDV infection; and
  (b) collecting the progeny virus,
  wherein the virus is grown to sufficient quantities and under sufficient conditions that the virus is free from contaraination, such that the progeny virus is suitable for formulation into a pharmaceutical composition.

14. A method for producing a pharmaceutical composition, the method comprising:
  (a) propagating the chimeric NDV of claim 1 in an isolated embryonated chicken or quail egg: and
  (b) collecting the progeny virus,
  wherein the virus is grown to sufficient quantities and under sufficient conditions that the virus is free from contamination, such that the progeny virus is suitable for formulation into a pharmaceutical composition.

* * * * *